United States Patent
Kubo

(10) Patent No.: US 9,595,117 B2
(45) Date of Patent: Mar. 14, 2017

(54) IMAGE PROCESSING DEVICE AND METHOD FOR OPERATING ENDOSCOPE SYSTEM

(71) Applicant: FUJIFILM Corporation, Tokyo (JP)

(72) Inventor: Masahiro Kubo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 183 days.

(21) Appl. No.: 14/192,505

(22) Filed: Feb. 27, 2014

(65) Prior Publication Data

US 2014/0253580 A1    Sep. 11, 2014

(30) Foreign Application Priority Data

Mar. 6, 2013  (JP) ................................. 2013-044046

(51) Int. Cl.
*G06T 11/00* (2006.01)
*G06T 5/00* (2006.01)

(52) U.S. Cl.
CPC ............ *G06T 11/001* (2013.01); *G06T 5/007* (2013.01); *G06T 2207/10024* (2013.01); *G06T 2207/10068* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 2005/0100208 A1* | 5/2005 | Suzuki | G06T 5/007 382/157 |
| 2012/0197076 A1 | 8/2012 | Minetoma | |
| 2012/0197077 A1* | 8/2012 | Kaku | A61B 1/00009 600/109 |
| 2013/0286172 A1* | 10/2013 | Sasaki | A61B 1/00009 348/65 |

FOREIGN PATENT DOCUMENTS

| | | |
|---|---|---|
| JP | 2002-165757 A | 6/2002 |
| JP | 3559755 B2 | 9/2004 |

(Continued)

OTHER PUBLICATIONS

Japanese Office Action and English translation thereof, dated May 6, 2016, for counterpart Japanese Application No. 2013-044046.

(Continued)

*Primary Examiner* — Kee M Tung
*Assistant Examiner* — Yi Wang
(74) *Attorney, Agent, or Firm* — Birch, Stewart, Kolasch & Birch, LLP

(57) ABSTRACT

A vessel suppression process is performed on RGB image data. A display of capillary vessels is suppressed by the vessel suppression process. After the vessel suppression process, tone of the RGB image data is reversed. Thereby, a suppressed-and-reversed image is produced. Even after the tone reversal, the capillary vessels do not interfere with observation of a ductal structure in the suppressed-and-reversed image, because the display of the capillary vessels is suppressed. In the suppressed-and-reversed image, the ductal structure is darker than a mucous membrane due to the tone reversal, so that the color of the ductal structure is close to that of an indigo.

15 Claims, 19 Drawing Sheets

(56) References Cited

FOREIGN PATENT DOCUMENTS

| JP | 3572304 B2 | 9/2004 |
| JP | 3607857 B2 | 1/2005 |
| JP | 2009-66147 A | 4/2009 |
| JP | 4451460 B2 | 4/2010 |
| JP | 2012-152459 A | 8/2012 |

OTHER PUBLICATIONS

Chinese Office Action and English translation thereof, dated Jul. 26, 2016 for counterpart Chinese Application No. 201410072131.0.

* cited by examiner

DUCTAL STRUCTURE S

DUCTAL STRUCTURE S

DUCTAL STRUCTURE S

CAPILLARY VESSELS V

DUCTAL STRUCTURE S

CAPILLARY VESSELS V

DUCTAL STRUCTURE S

CAPILLARY VESSELS V

DUCTAL STRUCTURE S

CAPILLARY VESSELS V

DUCTAL STRUCTURE S

CAPILLARY VESSELS V

DUCTAL STRUCTURE S

CAPILLARY VESSELS V

DUCTAL STRUCTURE S

DUCTAL STRUCTURE S

DUCTAL STRUCTURE S

CAPILLARY VESSELS V

DUCTAL STRUCTURE S

CAPILLARY VESSELS V

IMAGE PROCESSING DEVICE AND METHOD FOR OPERATING ENDOSCOPE SYSTEM

BACKGROUND OF THE INVENTION

1. Field of the Invention

The present invention relates to an image processing device and a method for operating an endoscope system, for performing diagnoses based on observation of a ductal structure and the like in a human body.

2. Description Related to the Prior Art

Diagnoses using endoscope systems are widely performed in current medical care. The endoscope system comprises a light source device, an electronic endoscope, and a processor device. Observation of a human body cavity is performed using the endoscope system. Such observation includes screening observation and magnified observation. In the screening observation, a potential lesion (site with a high possibility of being a lesion) such as a brownish area or redness is detected from a far view. The magnified observation is performed in a case where the potential lesion is detected. In the magnified observation, the endoscope zooms in on the potential lesion. Thereby the potential lesion is magnified and examined. Diagnosis is performed based on the observation of a ductal structure.

In the magnified observation of the ductal structure, the contrast of the ductal structure S is low in a normal image (an image captured with the illumination of the white light). It is difficult to interpret the state of the ductal structure S. In this case, a dye such as an indigo is sprayed. The dye deposits on pits of the ductal structure S. Thereby the contrast of the ductal structure S is improved. The sprayed dye makes the ductal structure S conspicuous, allowing interpretation of the state of the ductal structure S.

The ductal structure S is enhanced with a white color in a displayed image by illuminating the ductal structure S with blue narrowband light of narrowband wavelengths in a blue region. This is due to the fact that the narrowband light tends to be reflected around a surface layer of a mucous membrane. The contrast of the ductal structure S improves in a blue narrowband image captured with the illumination of the blue narrowband light, allowing the interpretation of the state of the ductal structure S (see Japanese Patent No. 3607857).

In narrowband light observation using the blue narrowband light, the structure of the ductal structure S is enhanced without spraying the dye. Washing of the dye is unnecessary, which reduces the burden of a doctor. The ductal structure S in the narrowband light observation is displayed in whitish colors. The dye-sprayed ductal structure S is displayed in bluish colors. The color of the ductal structure S in the narrowband light observation is totally different from the color of the dye-sprayed ductal structure S when displayed. The doctor who is accustomed to the dye observation has difficulties in observing the ductal structure S displayed in a color different from that of the dye such as the indigo.

For this reason, it is desirable to display the ductal structure S in colors close to the color of the dye such as the indigo, even in the narrowband light observation. For example, in the Japanese Patent No. 3607857, the blue narrowband image is assigned to RGB channels (ch) of a monitor. A weighting factor for the B ch is made greater than those for the G ch and R ch. Thereby the ductal structure S is displayed in colors similar to those of the dye-sprayed one. In this case, however, not only the ductal structure S but also the capillary vessels are displayed in indigo colors. A difference between the ductal structure S and the capillary vessels is not obvious and cannot be enhanced.

The ductal structure displayed brightly in white color may be partially darkened by a tone reversal process disclosed in Japanese Patent Laid-Open Publication No. 2009-066147 and Japanese Patent Nos. 4451460, 3572304, and 3559755. Thereby the ductal structure is made conspicuous in a manner similar to the indigo spraying. However, the tone reversal process is applied to every pixel in the image. The tone of a vascular structure is reversed in addition to that of the ductal structure.

For example, when the tone reversal process is performed on a narrowband image (an image in which both the ductal structure S and the capillary vessels V are enhanced in the display due to the application of the blue narrowband light) produced in the narrowband light observation, the capillary vessels V are highlighted and as conspicuous as the ductal structure S as shown by a reversed narrowband image shown in FIG. 24A. In FIG. 24B, black thick lines are added to the image of FIG. 24A displayed on the monitor, to indicate the ductal structure S. The conspicuous blood vessels impair visual recognition properties of the ductal structure S and make it difficult to accurately interpret the state of the ductal structure S. Thus, it is necessary to enhance the display of the ductal structure without making the blood vessels conspicuous.

Note that the Japanese Patent No. 3572304 discloses that the blood vessels are clearly displayed by the tone reversal process. However, neither of the above-mentioned documents including the Japanese Patent No. 3572304 touches upon displaying the ductal structure with high clarity in the narrowband light observation and enhancing the ductal structure in the display without making the blood vessels conspicuous.

SUMMARY OF THE INVENTION

An object of the present invention is to provide an image processing device and a method for operating an endoscope system, capable of an enhanced display of a ductal structure without making blood vessels conspicuous.

An image processing device of the present invention comprises an image input section and a suppression and reversal section. The image input section inputs a first image. The first image includes a first structure and a second structure darker than the first structure. The suppression and reversal section performs a suppression process and a tone reversal process on the first image to produce a second image. A display of the second structure is suppressed in the suppression process. The first structure is darker than the second structure in the second image.

It is preferable that the first structure is brighter than a mucous membrane and the second structure is darker than the mucous membrane in the first image, and the suppression and reversal section comprises a suppression section and a first tone reversal section. The suppression section performs the suppression process on the first image. The first tone reversal section performs the tone reversal process on a suppression-processed first image to make the first structure darker than the mucous membrane. It is preferable that the first image is represented by RGB image data, and the first tone reversal section reverses a tone of suppression-processed RGB image data.

It is preferable that the image processing device further comprises a separator for separating the suppression-processed first image into brightness data and color data. The brightness data has brightness information. The color data has color information. It is preferable that the first tone reversal section reverses the tone of the brightness data.

In the first image, the first structure is brighter than a mucous membrane and the second structure is darker than the mucous membrane. It is preferable that the suppression and reversal section comprises a suppression section and a second tone reversal section. The suppression section performs the suppression process on the first image. The second tone reversal section performs the tone reversal process on a suppression-processed first image to make the first structure darker than the mucous membrane and to make the color of the first structure close to a color of a bluish dye. It is preferable that the tone reversal process of the second tone reversal section makes a color of the mucous membrane close to a color of the mucous membrane illuminated with white light.

It is preferable that the first image is represented by RGB image data, and the second tone reversal section reverses a tone of suppression-processed R image data so as to make an intermediate value of the suppression-processed R image data bright, and reverses atone of suppression-processed B image data so as to make an intermediate value of the suppression-processed B image data dark, and reverses the tones such that dark portions become bright after the tone reversal process. It is preferable that the image processing device further comprises a separator for separating the suppression-processed first image into brightness data and color data. The brightness data has brightness information. The color data has color information. It is preferable that the second tone reversal section reverses a tone of the brightness data so as to make an intermediate value of the brightness data bright, and changes the color data so as to make an yellowish color close to blue. It is preferable that the bluish dye is an indigo.

It is preferable that the first image has a blue narrowband image which includes the first and the second structures. It is preferable that the image processing device further comprises an image magnifying section for magnifying the first and the second structures. It is preferable that the first image is obtained in magnified observation using the image magnifying section. It is preferable that the first structure is a ductal structure and the second structure is capillary vessels.

A method for operating an endoscope system of the present invention comprises an inputting process and a producing process. In the inputting process, a first image is inputted from an image input section. The first image includes a first structure and a second structure darker than the first structure. In the producing step, a suppression and reversal section performs a suppression process and a tone reversal process on the first image to produce a second image. A display of the second structure is suppressed in the suppression process. The first structure is darker than the second structure in the second image.

According to the present invention, the ductal structure is enhanced in the display with the blood vessels being inconspicuous.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
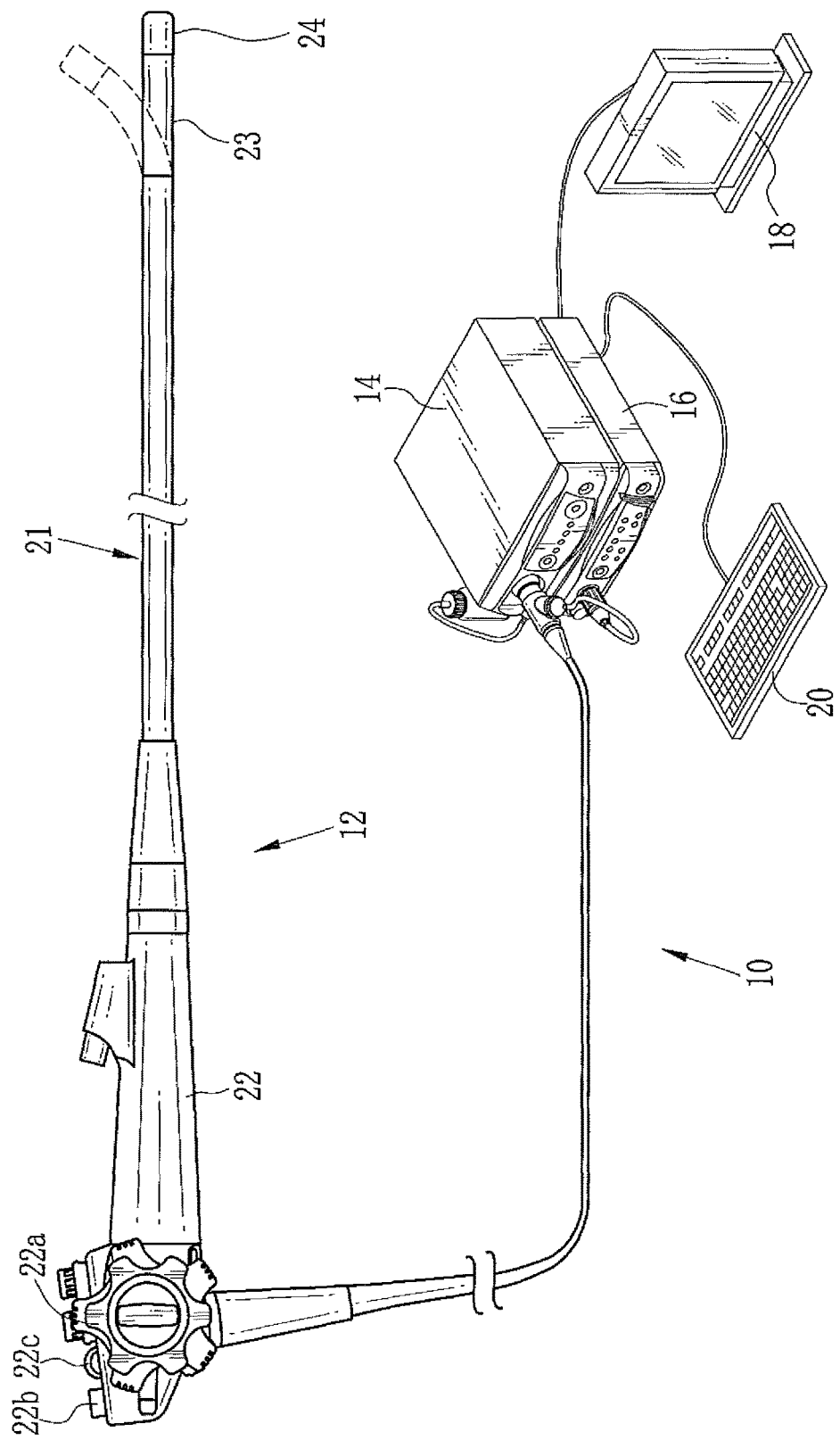
FIG. 1 is an external view of an endoscope system.

As shown in FIG. 1, an endoscope system 10 according to a first embodiment has an endoscope 12, a light source device 14, a processor device 16, a monitor 18, and a console 20. The endoscope 12 is optically connected to the light source device 14. The endoscope 12 is electrically connected to the processor device 16. The endoscope 12 has an insert section 21, a handle section 22, a bending portion 23, and a distal portion 24. The insert section 21 is inserted in a body cavity. The handle section 22 is provided in a proximal portion of the insert section 21. The bending portion 23 and the distal portion 24 are provided on a distal side of the insert section 21. The bending portion 23 is bent by operating an angle knob 22a of the handle section 22. The bending portion 23 is bent to direct the distal portion 24 to a desired direction.

In addition to the angle knob 22a, the handle section 22 is provided with a mode selection SW (switch) 22b and a zoom operation section 22c. The mode selection SW 22b is used to switch among three modes: a normal mode, a first special mode, and a second special mode. White light is used in the normal mode. Bluish special light is used in the first and the second special modes. In the first special mode, both of a ductal structure and capillary vessels are clearly displayed. In the second special mode, the ductal structure is displayed clearly while the display of the blood vessels is suppressed. The zoom operation section 22c drives a zooming lens 47 (see FIG. 2), which is provided in the endoscope 12, to perform zoom operation for magnifying an observation object.

The processor device 16 is electrically connected to the monitor 18 and the console 20. The monitor 18 outputs and displays image information and the like. The console 20 functions as a UI (user interface) for accepting input operation such as setting a function. Note that external storage (not shown) may be connected to the processor device 16. The image information and the like is recorded in the external storage.

Figure 2:
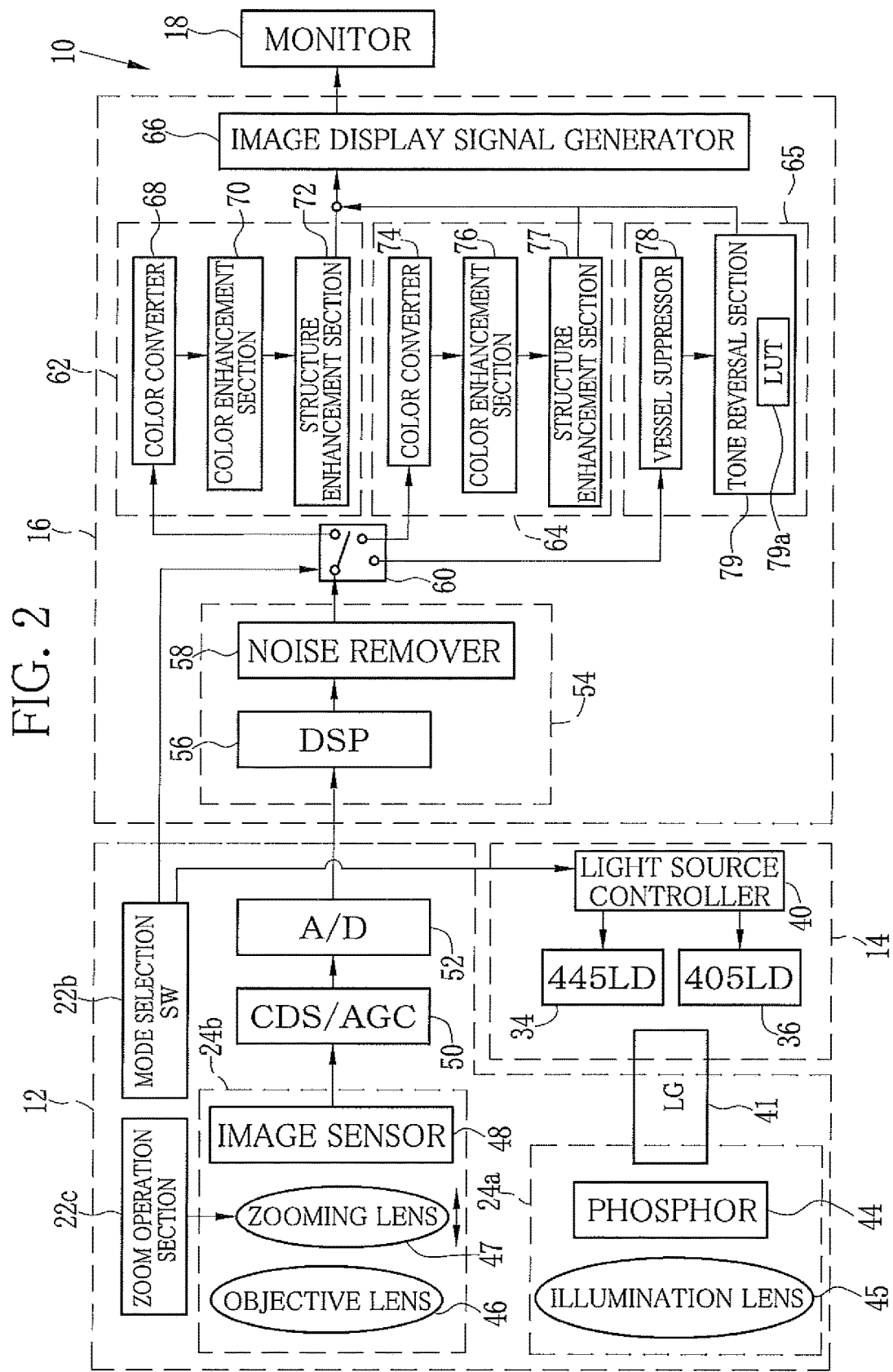
FIG. 2 is a block diagram illustrating configuration of an endoscope of a first embodiment.

As shown in FIG. 2, the light source device 14 comprises a blue laser (445LD) 34 and a blue-violet laser (405LD) 36 as light sources. The blue laser 34 emits blue laser beams with the center wavelength of 445 nm. The blue-violet laser 36 emits blue-violet laser beams with the center wavelength of 405 nm. A light source controller 40 separately controls light emissions from semiconductor light emitting elements of the respective lasers 34 and 36. A light quantity ratio between the emission beams from the blue laser 34 and the emission beams from the blue-violet laser 36 is changed as desired. In the normal mode, the light source controller 40 mainly drives the blue laser 34 such that a slight quantity of the blue-violet laser beams is emitted. In the first and the second special modes, the light source controller 40 drives both of the blue laser 34 and the blue-violet laser 36 such that the light quantity of the blue-violet laser beams is greater than that of the blue laser beams.

Note that it is preferable that full width at half maximum of the blue laser beams or the blue-violet laser beams is in the order of ±10 nm. In the normal mode, the blue-violet laser 36 may be turned off. The blue laser 34 and the blue-violet laser 36 may be broad-area InGaN laser diodes, InGaNAs laser diodes, or GaNAs laser diodes. A light emitter such as a light emitting diode may be used as the above-described light source.

The laser beams emitted from the laser 34 or 36 are incident on a light guide (LG) 41 through optical members such as a condenser lens, an optical fiber, and a combiner (all not shown). The light guide 41 is incorporated in a universal cord (not shown), which connects the light source device 14 and the endoscope 12. The blue laser beams with the center wavelength of 445 nm or the blue-violet laser beams with the center wavelength of 405 nm propagate through the light guide 41 to the distal portion 24 of the endoscope 12. Note that a multi-mode fiber may be used as the light guide 41. For example, a small-diameter fiber cable with a core diameter of 105 μm and a clad diameter of 125 μm may be used. The total diameter φ=0.3-0.5 mm. The total diameter φ of the fiber cable includes a protection layer, being an outer sheath.

The distal portion 24 of the endoscope 12 has an illuminating optical system 24a and an imaging system 24b. The illuminating optical system 24a is provided with a phosphor 44 and an illumination lens 45. The blue laser beams with the center wavelength of 445 nm or the blue-violet laser with the center wavelength of 405 nm are incident on the phosphor 44 from the light guide 41. Fluorescence is emitted from the phosphor 44 by the application of the blue laser beams. A part of the blue laser beams passes through the phosphor 44. The blue-violet laser beams passes through the phosphor 44 without exciting the phosphor 44. The light from the phosphor 44 is applied to the observation object through the illumination lens 45.

Figure 3A:
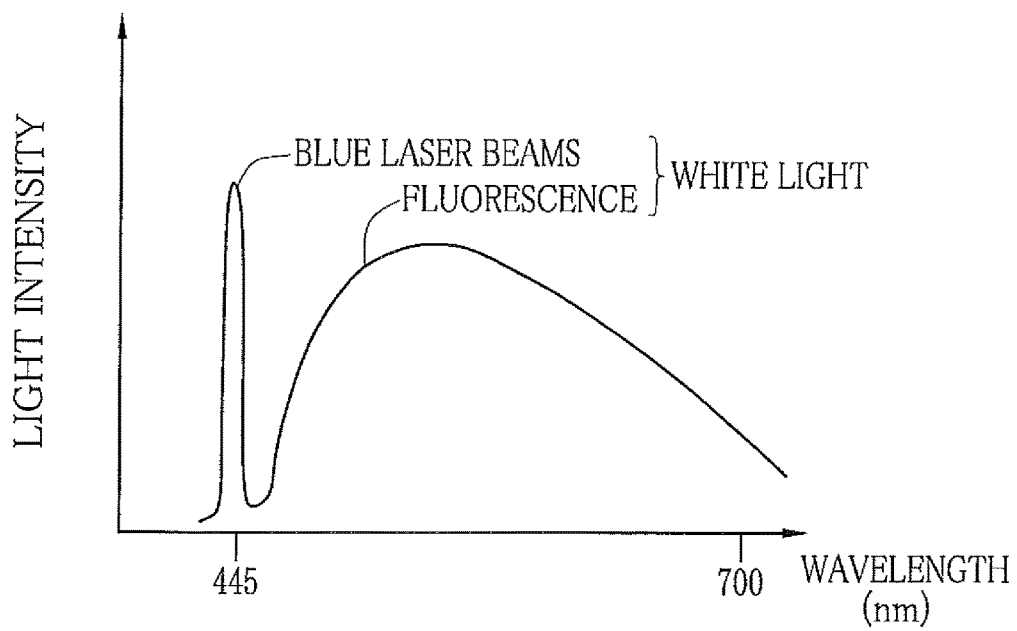
FIG. 3A is a graph illustrating emission spectra of white light.
Figure 3B:
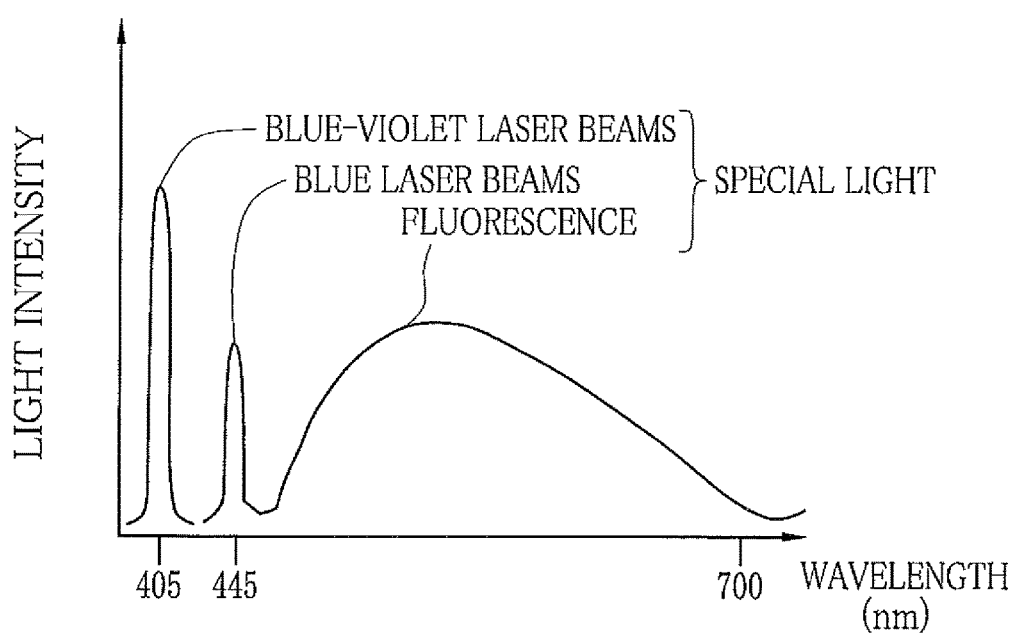
FIG. 3B is a graph illustrating emission spectra of special light.

In the normal mode, the blue laser beams are mainly incident on the phosphor 44. Thereby, as shown in FIG. 3A, white light is applied to the observation object. The white light is produced by mixing the blue laser beams and the fluorescence. The fluorescence is emitted from the phosphor 44 which is excited by the blue laser beams. In the first and the second special modes, both of the blue-violet laser beams and the blue laser beams are incident on the phosphor 44. Hence, as shown in FIG. 3B, the special light is applied to the observation object. The special light is produced by mixing the blue-violet laser beams, the blue laser beams, and the fluorescence emitted from the phosphor 44 excited by the blue laser beams. In the first and the second special modes, the light quantity of the blue-violet laser beams is greater than that of the blue laser beams. Hence, the special light contains a high proportion of blue components, and the wavelength range of the special light covers substantially the entire visible light region.

Note that it is preferable to use the phosphor 44 composed of two or more fluorescent substances (for example, YAG fluorescent substances or BAM(BaMgAl$_{10}$O$_{17}$)) which absorb a part of the blue laser beams to emit light of green to yellow. As described in this embodiment, with the use of the semiconductor light emitting element as the excitation light source for the phosphor 44, the white light with high intensity is emitted with high light emission efficiency. The intensity of the white light is adjusted easily. Fluctuations in color temperature and chromaticity of the white light are suppressed to a small extent.

As shown in FIG. 2, the imaging system 24b of the endoscope 12 has an objective lens 46, the zooming lens 47, and an image sensor 48, being an image input section. Light reflected from the observation object is incident on the image sensor 48 through the objective lens 46 and the zooming lens 47. Thereby an image of the observation object is formed on the image sensor 48. The zooming lens 47 is moved between a telephoto end and a wide-angle end by operating the zoom operation section 22c. The reflection image of the observation object is magnified when the zooming lens 47 is moved to a wide-angle end side. The reflection image of the observation object is reduced when the zooming lens 47 is moved to a telephoto end side. The zooming lens 47 is used as an image magnifying section to optically change the magnification of the image. Alternatively, the image magnification may be changed electrically.

The image sensor 48 is a color image sensor. The image sensor 48 captures a reflection image of the observation object and outputs image signals. Note that the image sensor 48 is preferably a CCD (Charge Coupled Device) image sensor, a CMOS (Complementary Metal-Oxide Semiconductor) image sensor, or the like. The image sensor used in the present invention may be an RGB image sensor or a complementary image sensor. The RGB image sensor has an RGB mosaic filter on its imaging surface to obtain image signals of three colors, R (red), G (green), and B (blue). An imaging surface of the complementary color image sensor is provided with a complementary color mosaic filter of C (cyan), M (magenta), Y (yellow), and G (green). Even if the complementary color image sensor is used, the image signals which represent luminance values of the three colors (RGB), respectively, are obtained by color conversion of the image signals of four colors (CMYG). In this case, it is necessary that one of the endoscope 12, the light source device 14, and the processor device 16 comprises a color converter for converting the image signals of four colors (CMYG) into the image signals of three colors (RGB).

The image signal outputted from the image sensor 48 is transmitted to a CDS/AGC circuit 50. The CDS/AGC circuit 50 performs correlated double sampling (CDS) and automatic gain control (AGC) on the image signal (analog signal). An A/D converter 52 converts the image signal which has passed through the CDS/AGC circuit 50 into a digital image signal. The A/D converted digital image signal is inputted to the processor device 16.

The processor device 16 comprises a receiver 54, an image processor selector 60, a normal image processor 62, a first special image processor 64, a second special image processor 65, and an image display signal generator 66. The receiver 54 receives the digital image signal from the endoscope 12. The receiver 54 comprises a DSP (Digital Signal Processor) 56 and a noise remover 58. The DSP 56 performs gamma correction and color correction processing on the digital image signal. The noise remover 58 performs noise removal process (for example, moving average method, median filter method, or the like) on the digital image signal which has been subjected to the gamma correction and the like in the DSP 56. Thereby noise is removed from the digital image signal. The digital image signal from which noise has been removed is transmitted to the image processor selector 60.

In a case where the endoscope system 10 is set to the normal mode by the use of the mode selection SW 22b, the image processor selector 60 transmits the digital image signal to the normal image processor 62. In a case where the endoscope system 10 is set to the first special mode, the image processor selector 60 transmits the digital image signal to the first special image processor 64. In a case where the endoscope system 10 is set to the second special mode, the image processor selector 60 transmits the digital image signal to the second special image processor 65.

The normal image processor 62 has a color converter 68, a color enhancement section 70, and a structure enhancement section 72. The color converter 68 assigns the inputted digital image signals of three channels (R, G, and B) to R image data, G image data, and B image data, respectively. The RGB image data is subjected to color conversion processes such as a matrix process of 3×3, a tone reversal process, and a three-dimensional LUT process. Thereby the RGB image data is converted into color-converted RGB image data.

The color enhancement section 70 performs various color enhancement processes on the color-converted RGB image data. The structure enhancement section 72 performs structure enhancement processes for enhancing sharpness, edges, and the like on color-enhanced RGB image data. The RGB image data which has been subjected to the structure enhancement processes in the structure enhancement section 72 is inputted as a normal image to the image display signal generator 66.

The first special image processor 64 has a color converter 74, a color enhancement section 76, and a structure enhancement section 77. Of the digital image signals of the three RGB channels (ch), the color converter 74 assigns the G image signal to the R image data and assigns the B image signal to the G image data and the B image data. Here, the B image signal is assigned to the B image data. Instead of the G image signal, the B image signal is assigned to the G image data. Instead of the R image signal, the G image signal is assigned to the R image data. Hence, based on the RGB image data, a pseudo color image is displayed on the monitor 18. Note that the color converter 74 may assign the RGB image signals to the RGB image data, respectively, to produce an image based on white light, in a manner similar to the color converter 68.

Similar to the color enhancement section 70, the color enhancement section 76 performs various color enhancement processes on the color-converted RGB image data. Similar to the structure enhancement section 72, the structure enhancement section 77 performs the structure enhancement processes for enhancing sharpness, edges, and the like on the color-enhanced RGB image data. The RGB image data which has been subjected to the structure enhancement processes in the structure enhancement section 77 is inputted as a first special image to the image display signal generator 66.

The second special image processor 65 has a vessel suppressor 78 and a tone reversal section 79. The vessel suppressor 78 performs a vessel suppression process for suppressing the display of blood vessels on the inputted digital image signals of the three RGB channels, to produces a vessel-suppressed image. The tone reversal section 79 performs the tone reversal process for reversing the tone of the vessel-suppressed image, to produce a suppressed-and-reversed image. In the suppressed-and-reversed image, the display of the ductal structure is enhanced while the display of the blood vessels is suppressed.

Figure 4:
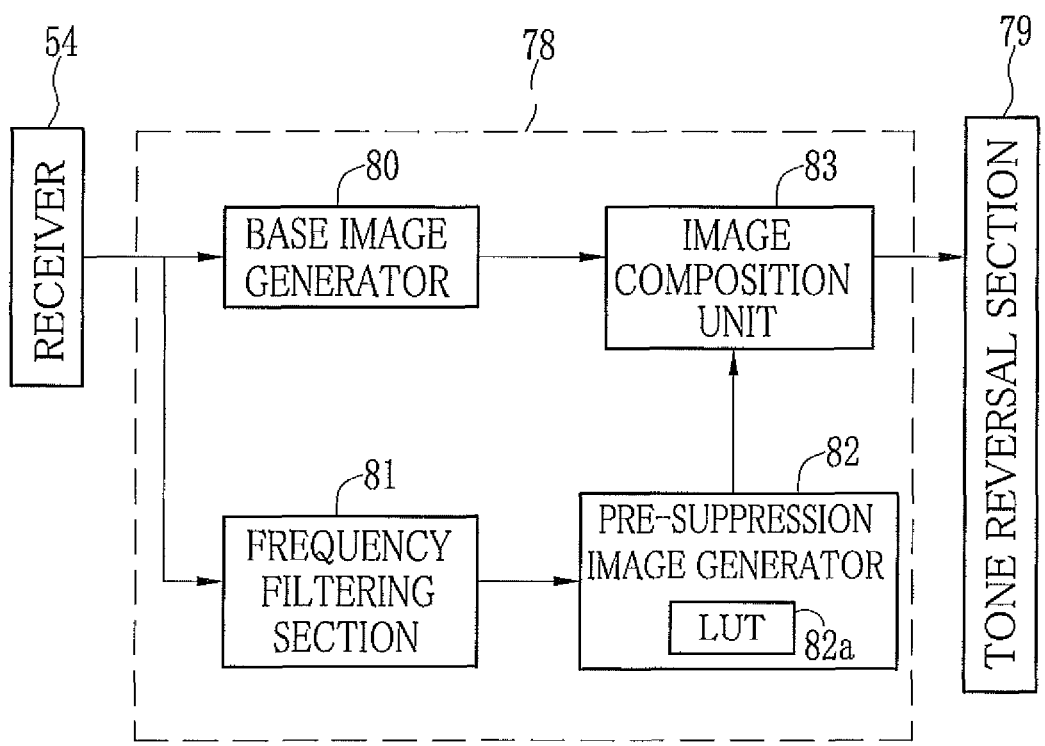
FIG. 4 is a block diagram illustrating each section in a vessel suppressor.

As shown in FIG. 4, the vessel suppressor 78 comprises a base image generator 80, a frequency filtering section 81, a pre-suppression image generator 82, and an image composition unit 83. Of the digital image signals of the three RGB channels, the base image generator 80 assigns the G image signal to the R image data and assigns the B image signal to the G image data and the B image data, in a manner similar to the color converter 74. Thus, the RGB image data forms a base image. The base image, being the first special image, is displayed in pseudo colors on the monitor 18. Note that, the base image generator 80 may assign the R, G, and B image signals to the respective RGB image data to produce an image based on white light, instead of the pseudo color image.

Figure 5:
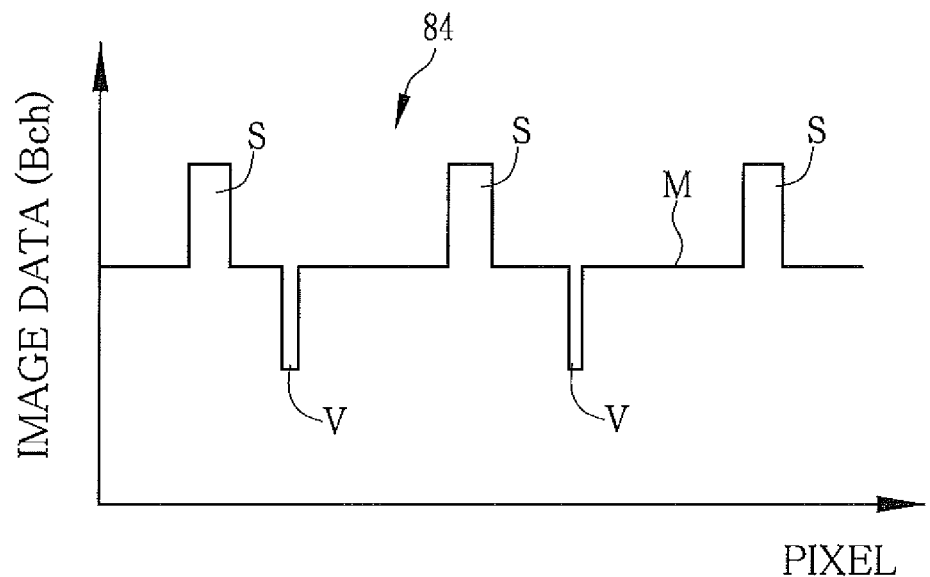
FIG. 5 is a graph illustrating luminance distribution along a predetermined line in a B image signal.

The B image data of the base image contains a high proportion of reflection components in a blue region, such as the blue-violet laser beams and the blue laser beams, which produce a structure enhancing effect on the ductal structure and the capillary vessels. Hence, as shown in FIG. 5, in B image data 84 of the base image, a ductal structure S is displayed brighter than a mucous membrane M, due to a high luminance value caused by the blue components of the light such as the blue-violet laser beams and the blue laser beams. The blue components of the light are likely to be reflected off around the surface layer of the mucous membrane on which the ductal structure S resides, resulting in high luminance. Unlike the blue narrowband light separated from broadband light such as xenon light, the blue-violet laser beams and the blue laser beams are highly rectilinear so that the beams reach the bottoms of pits in the ductal structure. Thereby, the ductal structure S is displayed brighter than that illuminated by the blue narrowband light. The capillary vessels V well-absorb the blue components such as the blue-violet laser beams and the blue laser beams, in which an extinction coefficient of hemoglobin is high, out of the special light. Hence, the capillary vessels V are displayed darker than the mucous membrane M.

Figure 6:
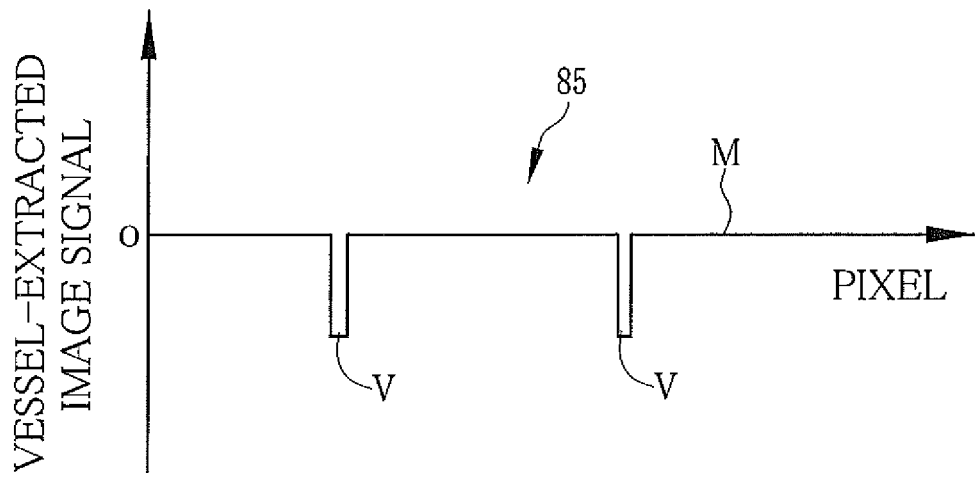
FIG. 6 is a graph illustrating luminance distribution along a predetermined line in a vessel-extracted image.

The frequency filtering section 81 performs a frequency filtering process on the B image signal of the digital image signals of the three RGB channels, to produce a vessel-extracted image signal. In the frequency filtering process, a frequency band component corresponding to the capillary vessels in the surface layer of the mucous membrane is extracted. As shown in FIG. 6, in a vessel-extracted image signal 85, the pixel corresponding to the capillary vessels V, which is included in the frequency band component extracted by the frequency filtering process, has a "negative" signal value (shown as a negative edge). The ductal structure S is not included in the frequency band component extracted by the frequency filtering process, so that a signal value of the pixel corresponding to the ductal structure S is approximately "0". There is substantially no change in luminance value of the mucous membrane M, so that a signal value of the pixel corresponding to the mucous membrane M is approximately "0". Note that, in order to enhance the ductal structure, the frequency band component is extracted so as to include both the frequency band corresponding to the ductal structure and the frequency band corresponding to the capillary vessels. In this case, the vessel-extracted image signal includes the pixel corresponding to the ductal structure having a "positive" signal value (positive edge).

The pre-suppression image generator 82 produces a pre-suppression image from the vessel-extracted image signal. The pre-suppression image is used for suppressing the display of the capillary vessels. The pre-suppression image generator 82 comprises an LUT 82a. The vessel-extracted image signal is inputted to the LUT 82a. The LUT 82a outputs a pre-suppression image signal. As shown by an input and output relationship in FIG. 7, the LUT 82a outputs a positive value in a case where the vessel-extracted image signal with a negative value is inputted. Thereby, as shown in FIG. 8, the pre-suppression image signal with "positive" pixel values corresponding to the capillary vessels V is obtained. The pre-suppression image signal is added to the base image. Thereby the brightness of the capillary vessels is close to the brightness of the mucous membrane. As a result, the contrast between the mucous membrane and the capillary vessels decreases or there may be substantially no difference between them.

Figure 7:
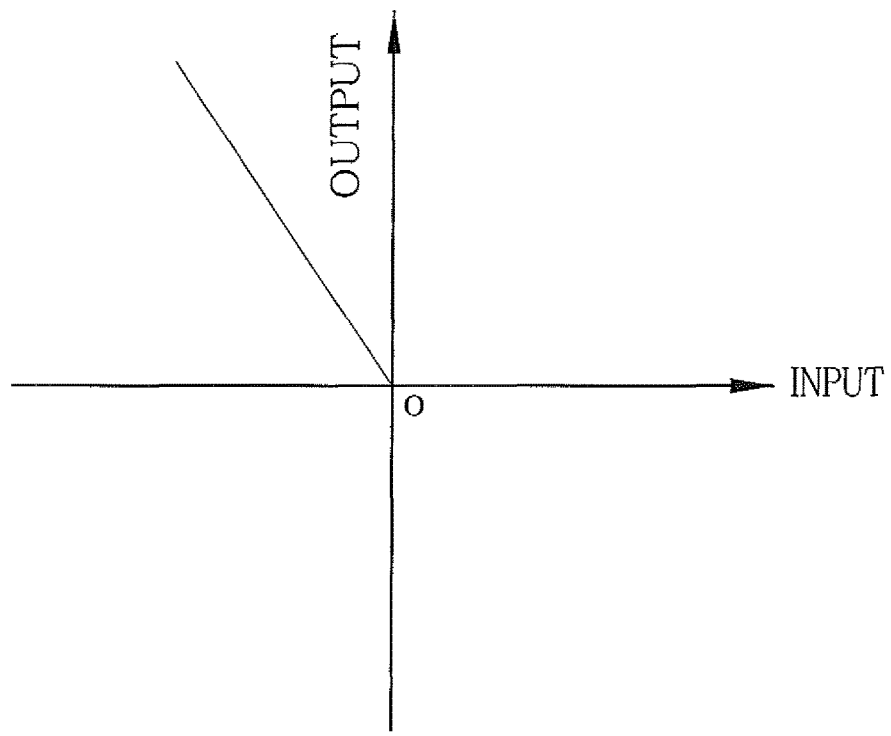
FIG. 7 is a graph illustrating an input-output relation of an LUT in a pre-suppression image generator.
Figure 8:
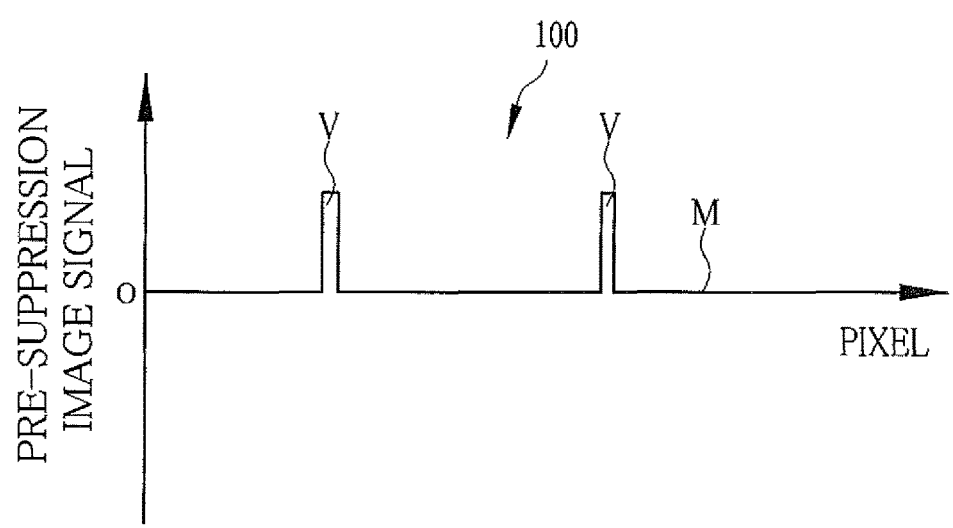
FIG. 8 is a graph illustrating luminance distribution along a predetermined line in a pre-suppression image.

Note that, as shown by the input and output relationship in FIG. 7, the LUT 82a outputs the pre-suppression image signal of "0" in a case where the vessel-extracted image signal with a positive value (positive edge) is inputted. The LUT 82a may output a "positive" value instead of "0" to enhance the ductal structure. In this case, the "positive" value is preferably increased in accordance with the degree of enhancement. The input and output relationship shown in FIG. 7 may be adjusted as necessary through the console 20. It is preferable to adjust the input and output relationship such that the pixel value corresponding to the capillary vessels becomes nearly equal to the pixel value corresponding to the mucous membrane when the pre-suppressed image signal is added to the image data of the base image.

The image composition unit 83 combines the pre-suppression image, which is produced from the pre-suppression image signal, with the base image. Thereby, a vessel-suppressed image, in which the display of the capillary vessels is suppressed, is produced. The image composition unit 83 adds pixel values of the pre-suppression image to the respective pixel values (B ch) of the B image data of the base image. The pixel values of the pre-suppression image may be added to the respective pixels of the G image data or the R image data. Note that the capillary vessels are preferably suppressed to an extent that the capillary vessels cannot be discriminated from the mucous membrane in the image, in other words, the capillary vessels disappear in the image as a result of combining the pre-suppression image with the base image.

Figure 9:
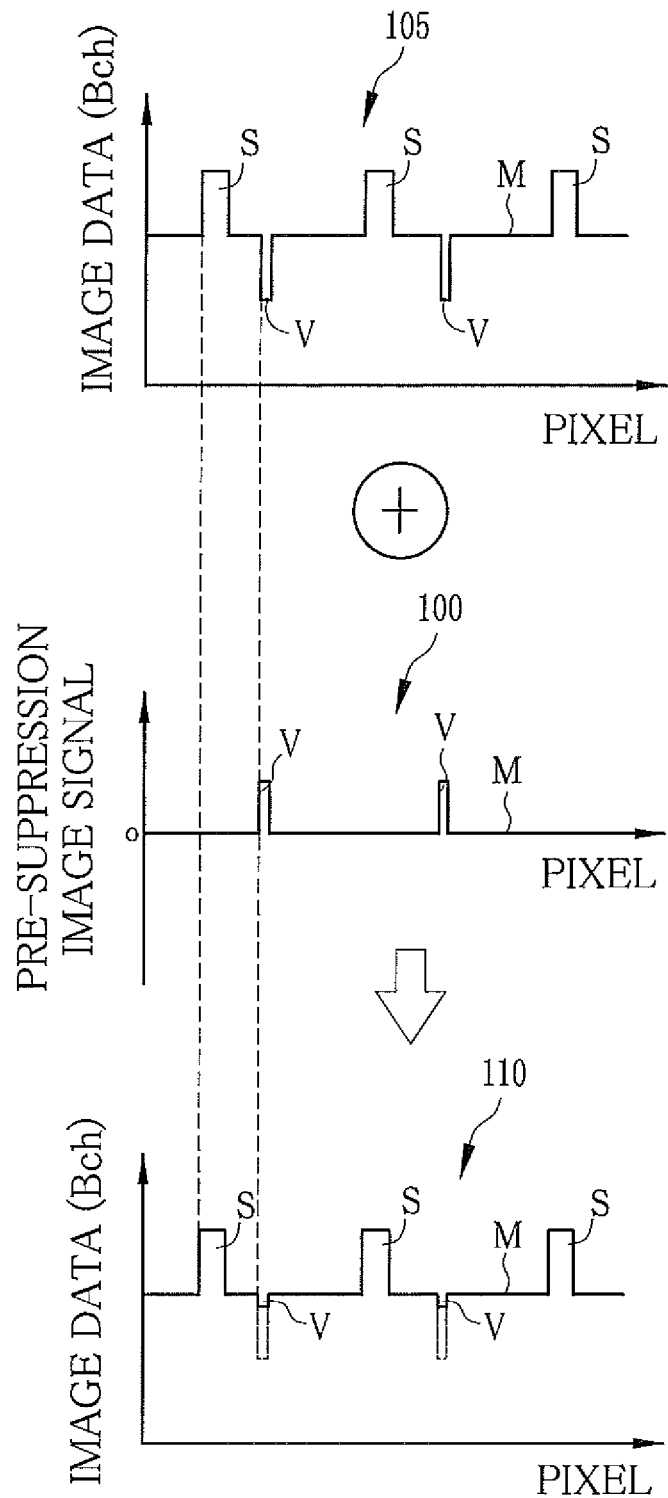
FIG. 9 is a graph illustrating luminance distribution along a predetermined line in a vessel-suppressed image, which is produced by combining the base image with the pre-suppression image.

For example, as shown in FIG. 9, the contrast between the capillary vessels V and the surrounding mucous membrane M is reduced by combining a vessel-suppressed image 100 (see FIG. 8) with B ch (respective pixels of the B image data) of a base image 105. Thereby, a vessel-suppressed image 110, in which the display of the capillary vessels V is suppressed, is produced. Dotted lines for the capillary vessels V denote luminance values before the image composition. Note that FIG. 9 illustrates the image composition of one line in the image.

Figure 10:
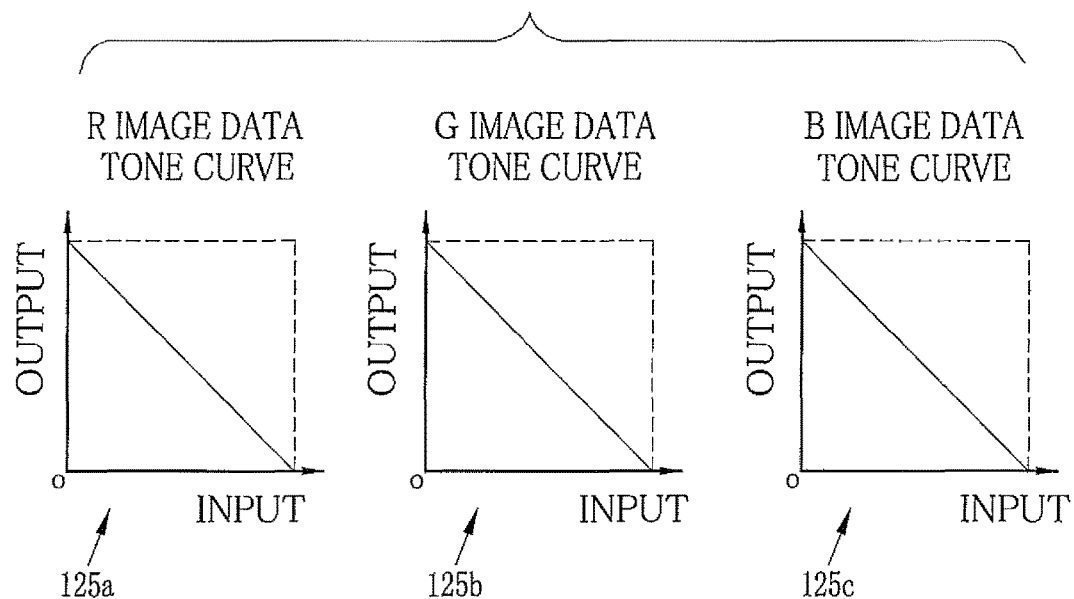
FIG. 10 illustrates graphs of tone curves for RGB image data, which are used for a tone reversal process of the first embodiment.

The tone reversal section 79 performs the tone reversal process on the RGB image data of the vessel-suppressed image inputted thereto. The tone reversal section 79 reverses the tone of the inputted RGB image data of the vessel-suppressed image, based on tone curves 125a to 125c for RGB image data shown in FIG. 10. Thereby the tone reversal section 79 outputs tone-reversed RGB image data of the suppressed-and-reversed image. Owing to the tone reversal process, brightness of a portion with an intermediate value is maintained as it is, while a bright portion becomes dark and a dark portion becomes bright. After the tone reversal process, the RGB image data of the suppressed-and-reversed image is transmitted as the second special image to the image display signal generator 66. Note that, data related to the tone curves 125a to 125c is stored in an LUT 79a in the tone reversal section 79.

Figure 11:
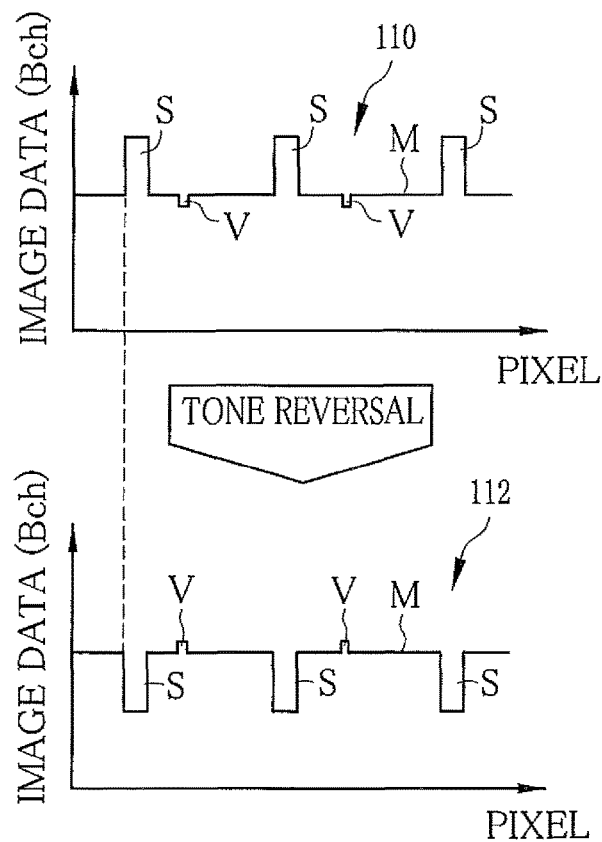
FIG. 11 is an explanatory view illustrating the tone reversal process.

For example, B image data of a suppressed-and-reversed image 112 shown in FIG. 11 is produced by performing the tone reversal process on the B image data of the vessel-suppressed image 110 (see FIG. 9). In the B image data of the suppressed-and-reversed image 112, the ductal structure S is darker than the mucous membrane M. Thus, by making the color of the ductal structure S darker than the color of the mucous membrane M in the suppressed-and-reversed image 112, the ductal structure S becomes conspicuous as if an indigo has been sprayed on the ductal structure S. The brightness of the capillary vessels V, on the other hand, is closer to that of the mucous membrane in the original image. Even after the tone reversal process, the tone-reversed capillary vessels V are slightly brighter than or as bright as the mucous membrane M in the suppressed-and-reversed image 112. Thus, the blood vessels do not interfere with visual recognition of the ductal structure in the suppressed-and-reversed image 112. A doctor who is accustomed to dye observation can interpret the state of the ductal structure easily.

Note that, instead of performing the tone reversal process on the RGB image data which represents the vessel-suppressed image, the tone reversal section 79 may separate the RGB image data of the vessel-suppressed image into brightness data and color data and may perform the tone reversal process only on the brightness data. After the tone reversal, the RGB conversion is performed on the color data and the tone-reversed brightness data. Thereby the RGB image data of the suppressed-and-reversed image produced.

Figure 12A:
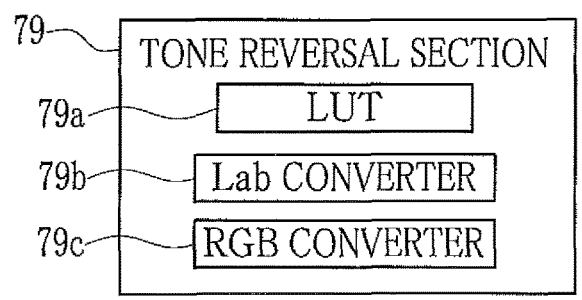
FIG. 12A is a block diagram illustrating a tone reversal section having a Lab converter and an RGB converter.
Figure 12B:
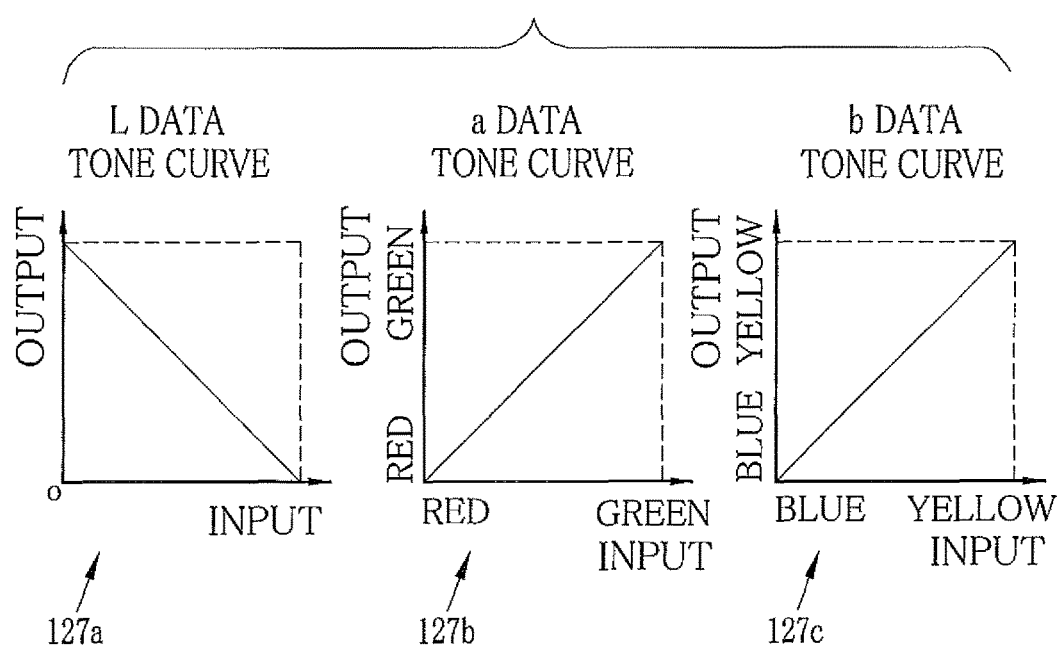
FIG. 12B illustrates graphs of tone curves for Lab data, which are used for the tone reversal process of the first embodiment.

For example, as shown in FIG. 12A, the tone reversal section 79 comprises a Lab converter 79b and an RGB converter 79c, to perform Lab conversion of the RGB image data which represents the vessel-suppressed image. First, the Lab converter 79b, being a separator, performs the Lab conversion on the RGB image data of the vessel-suppressed image, to separate the RGB image data into L data having brightness information, "a" data having color information related to red to green colors, and "b" data having color information related to blue to yellow colors. As shown in FIG. 12B, the tone of the L data is reversed based on a tone curve 127a. The tone of the "a" data and the color of the "b" data are maintained based on tone curves 127b and 127c. Thereby the color of the ductal structure S appears to be close to the color of the indigo which is darker than the color of the mucous membrane, without changing the color.

The RGB converter 79c performs the RGB conversion on the L data, the "a" data, and the "b" data. Thereby the RGB converter 79c converts the L data, the "a" data, and the "b" data into the RGB image data of the suppressed-and-reversed image. Note that the brightness data and the color data may be separated by YCbCr conversion instead of the Lab conversion. The data related to the tone curves 127a to 127c is stored in the LUT 79a in the tone reversal section 79.

The image display signal generator 66 converts each of a normal image inputted from the normal image processor 62, a first special image inputted from the first special image processor 64, and a second special image inputted from the second special image processor 65 into a display image signal. Thereby, the normal image and the first and second special images are displayable on the monitor 18. The monitor 18 displays the normal image, the first special image, and/or the second special image based on the respective display image signals.

Figure 13:
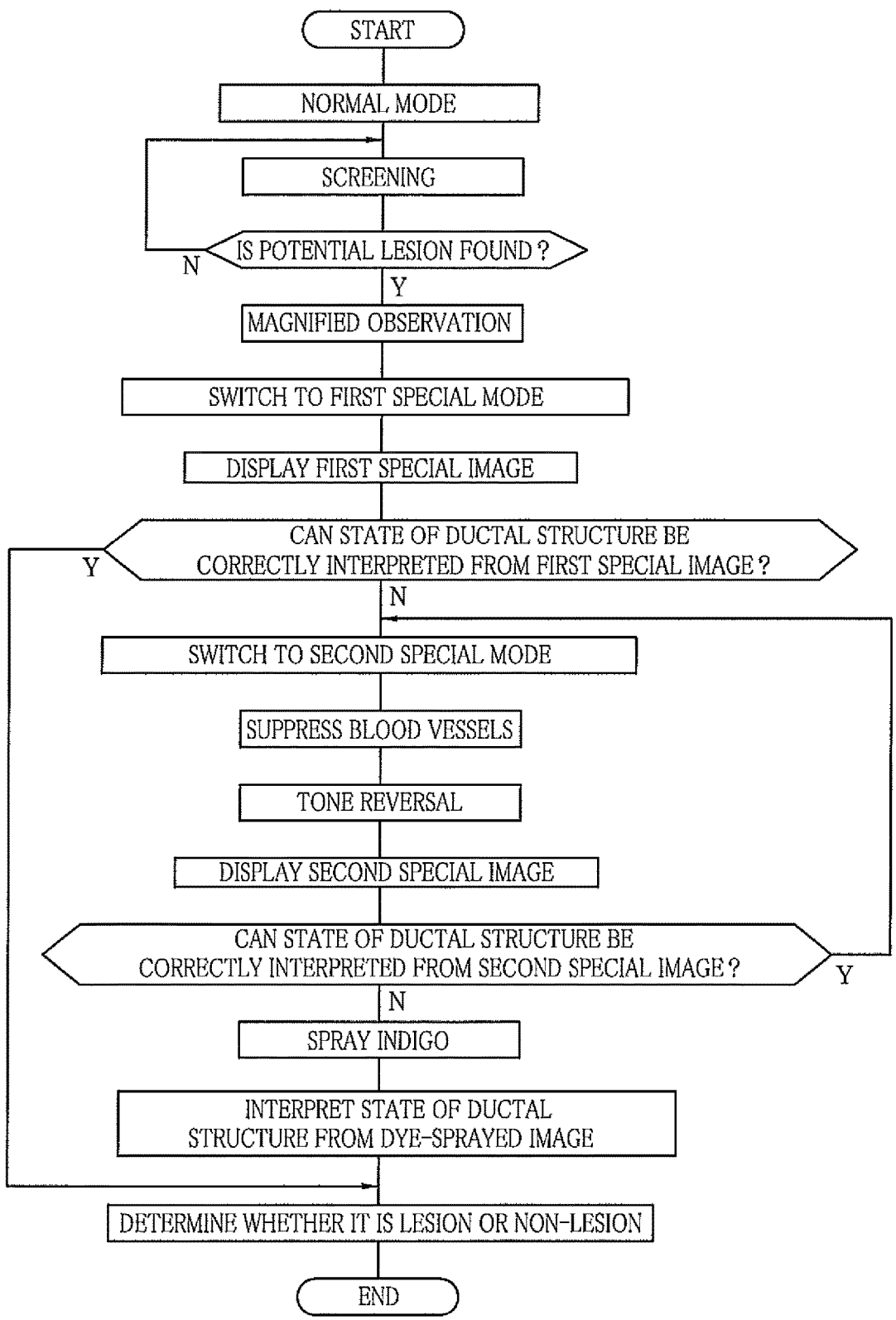
FIG. 13 is a flowchart illustrating a procedure in the first embodiment.
Figure 14A:
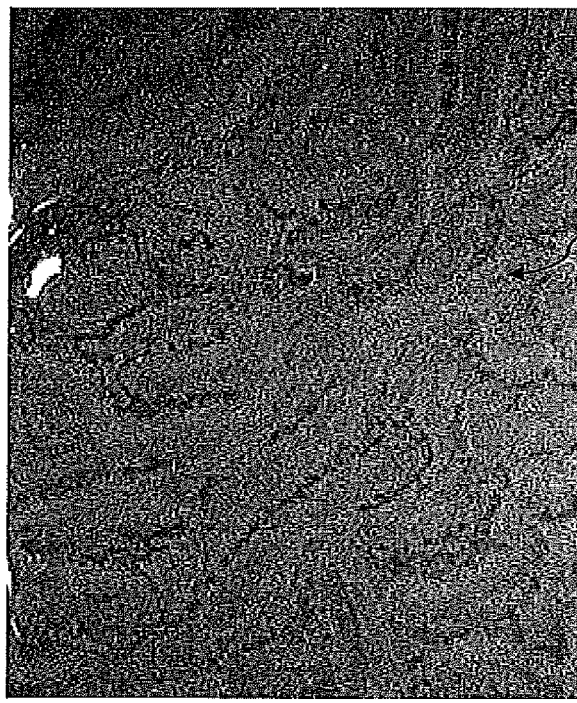
FIG. 14A illustrates an example of a normal image captured in magnified observation.

Next, an operation of this embodiment is described using a flowchart shown in FIG. 13. First, in the normal mode, screening of the observation object is performed in a far view. In a case where a potential lesion that is a site with a potentially malignant lesion, such as a brownish area or redness is detected, the zoom operation section 22c is operated to zoom in on the potential lesion. Thereby magnified observation in which the potential lesion is magnified is performed. In the magnified observation, a normal image with the ductal structure S magnified as shown in FIG. 14A is displayed on the monitor 18. In a case where the state of the ductal structure S in the normal image is accurately interpreted, whether the potential lesion is a lesion or a non-lesion is determined based on the normal image. Note that, in FIG. 14B, black thick lines are depicted to explicitly indicate the ductal structure S.

Figure 14B:
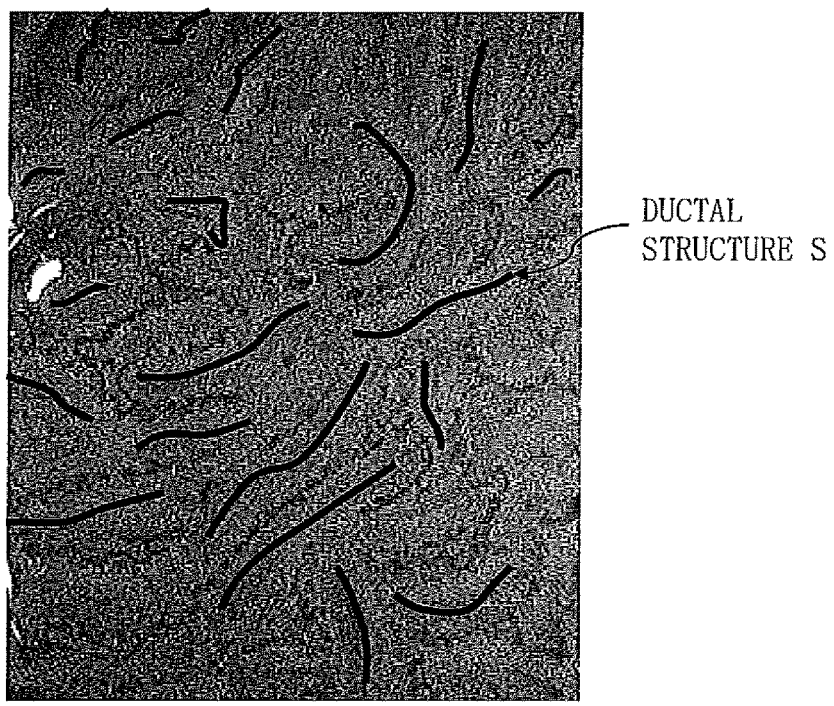
FIG. 14B is an explanatory image view in which black thick lines indicate a ductal structure of FIG. 14A.
Figure 15A:
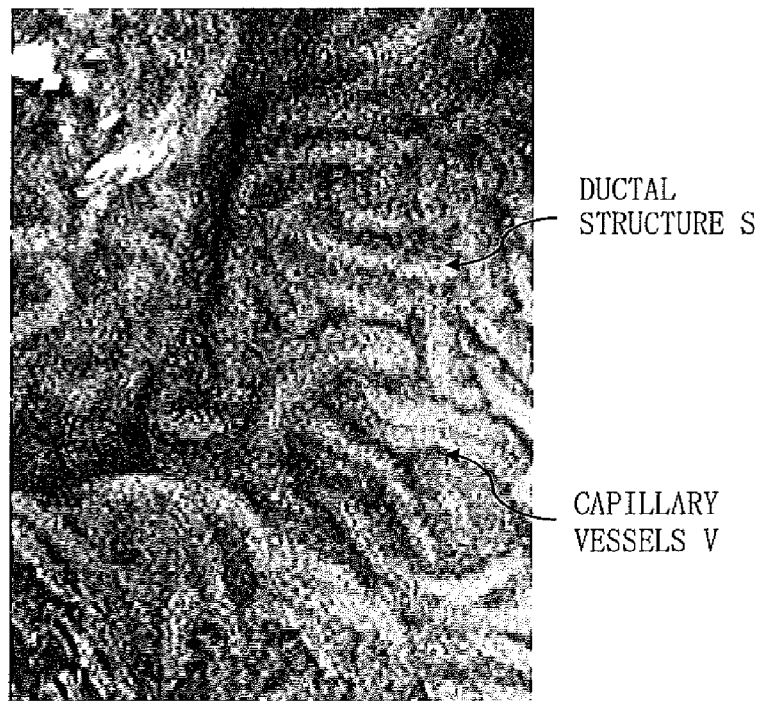
FIG. 15A illustrates an example of a first special image (narrowband image) captured in the magnified observation.
Figure 15B:
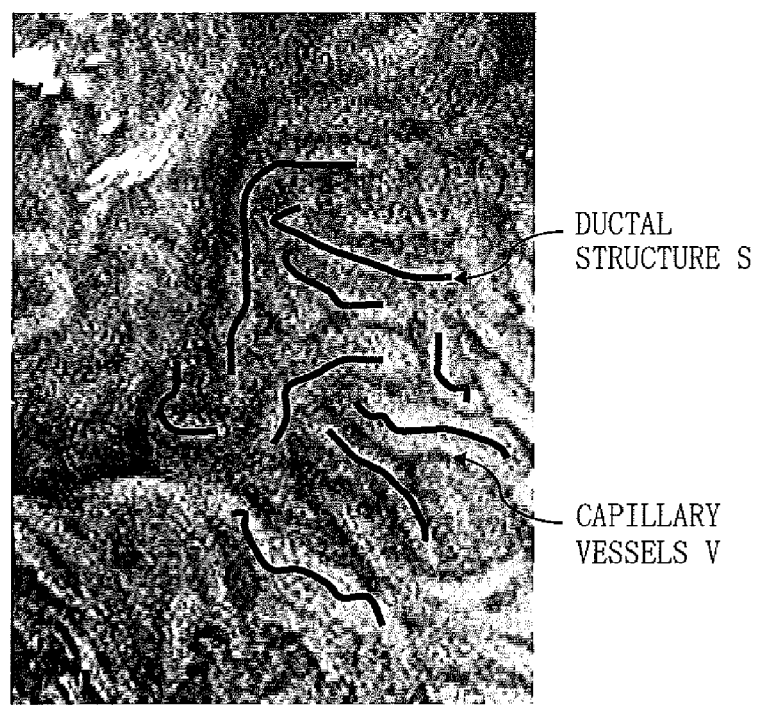
FIG. 15B an explanatory image view in which black thick lines indicate a ductal structure of FIG. 15A.

As is obvious from the comparison between the FIGS. 14A and 14B, it is generally difficult to accurately interpret the state of the ductal structure S in the normal image shown in FIG. 14A because the contrast of the ductal structure S is low. In most cases, the mode selection SW 22b is operated to switch the mode to the first special mode. Thereby, as shown in FIG. 15A, the first special image, in which the ductal structure S and the capillary vessels V are enhanced, is displayed on the monitor 18. Note that, in FIG. 15B, the black thick lines explicitly indicate the ductal structure S.

In a case where the state of the ductal structure S in the first special image is accurately interpreted, the doctor determines whether the potential lesion is a lesion or a non-lesion based on the first special image. The first special image shown in FIG. 15A is more useful than the normal image shown in FIG. 14A in interpreting the state of the ductal structure S because the ductal structure S is enhanced in the first special image. However, the first special image enhances both the ductal structure S and the capillary vessels V. The capillary vessels V may interfere with the visual recognition of the ductal structure S in a case where a part of the ductal structure S disappears. In this case, the state of the ductal structure S may not be interpreted accurately.

Figure 16A:
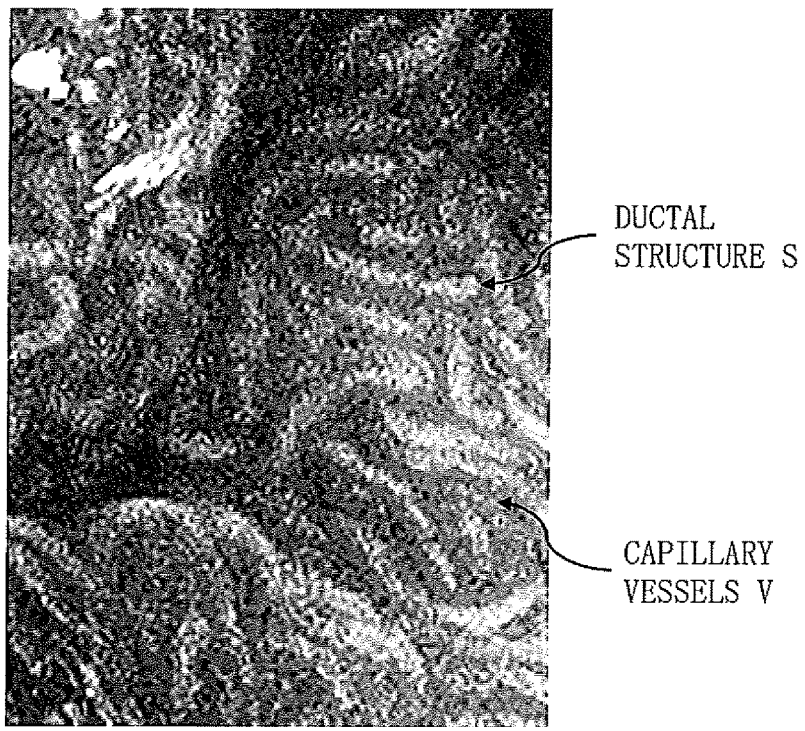
FIG. 16A illustrates an example of a vessel-suppressed image captured in the magnified observation.
Figure 16B:
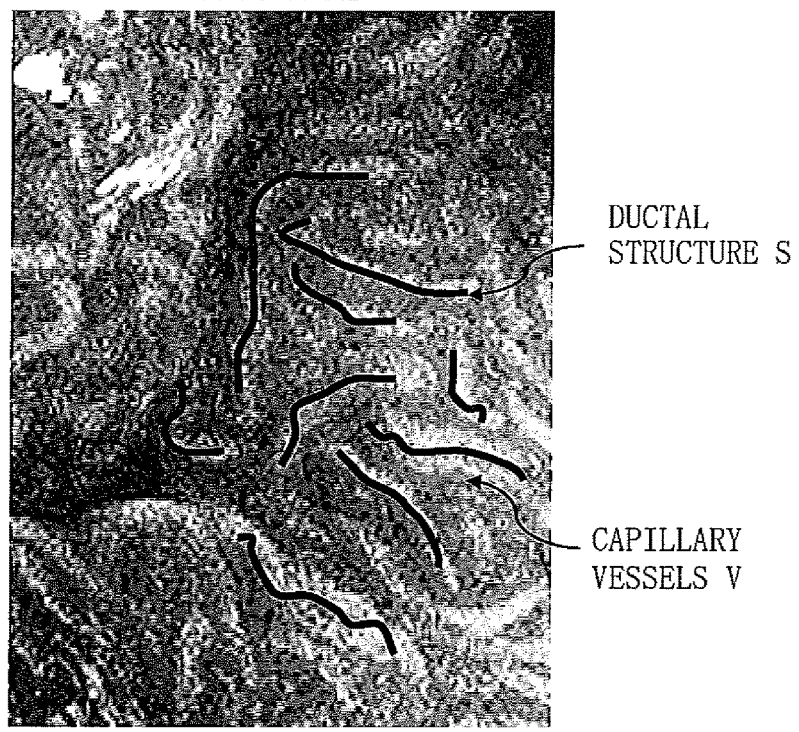
FIG. 16B is an explanatory image view in which black thick lines indicate a ductal structure of FIG. 16A.

In this case, the mode selection SW 22b is operated to switch from the first special mode to the second special mode. In the second special mode, first, the vessel suppressor 78 performs a process for suppressing the display of blood vessels, on the RGB image signals obtained by the image capture of the observation object. Thereby, as shown in FIG. 16A, the vessel-suppressed image, in which the display of the capillary vessels V is suppressed, is obtained. In the vessel-suppressed image, the capillary vessels V do not interfere with the visual recognition of the ductal structure S, as compared with the first special image shown in FIG. 15A. Thus, it is easy to interpret the state of the ductal structure S. Note that, in FIG. 16B, the black thick lines explicitly indicate the ductal structure S.

Figure 17A:
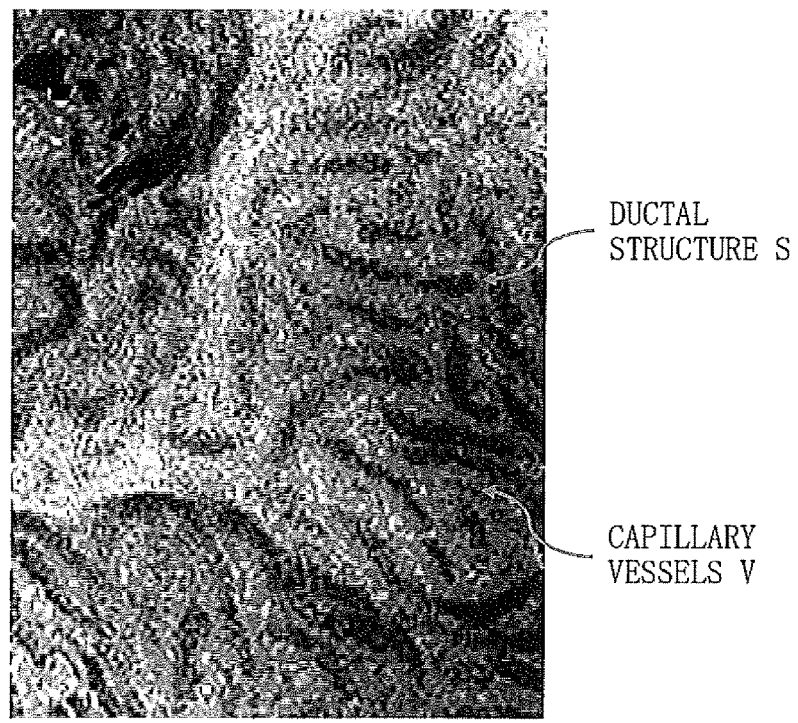
FIG. 17A illustrates a suppressed-and-reversed image captured in the magnified observation.
Figure 17B:
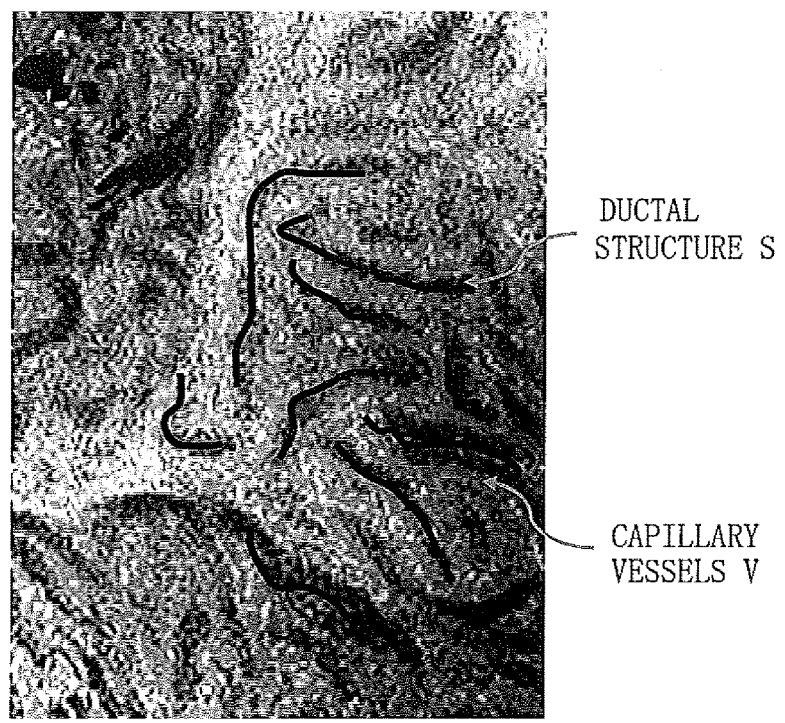
FIG. 17B is an explanatory image view in which black thick lines indicate a ductal structure of FIG. 17A.

The tone reversal section 79 performs the tone reversal process on the vessel-suppressed image. Thereby a suppressed-and-reversed image is obtained as shown in FIG. 17A. In the suppressed-and-reversed image, the contrast is improved by darkening the ductal structure S while the display of the capillary vessels V is suppressed. The suppressed-and-reversed image is displayed as the second special image on the monitor 18. In the second special image, the capillary vessels V do not interfere with the visual recognition of the ductal structure S because the display of the capillary vessels V has been suppressed. Furthermore, the ductal structure S is darkened, so that the color of the ductal structure S is close to the color of the indigo. Thus, the second special image is substantially the same as an image obtained by indigo spraying. The doctor who is accustomed to the dye observation can accurately interpret the state of the ductal structure without trouble. Note that, in FIG. 17B, the black thick lines explicitly indicate the ductal structure S.

In a case where the doctor can accurately interpret the state of the ductal structure S in the second special image, he/she determines whether the potential lesion is a lesion or a non-lesion based on the second special image. In a case where the state of the ductal structure S in the second special image cannot be accurately interpreted, a dye such as the indigo is sprayed as a last resort. Thereby the dye deposits on pit portions of the ductal structure S. As shown in FIG.

Figure 18A:
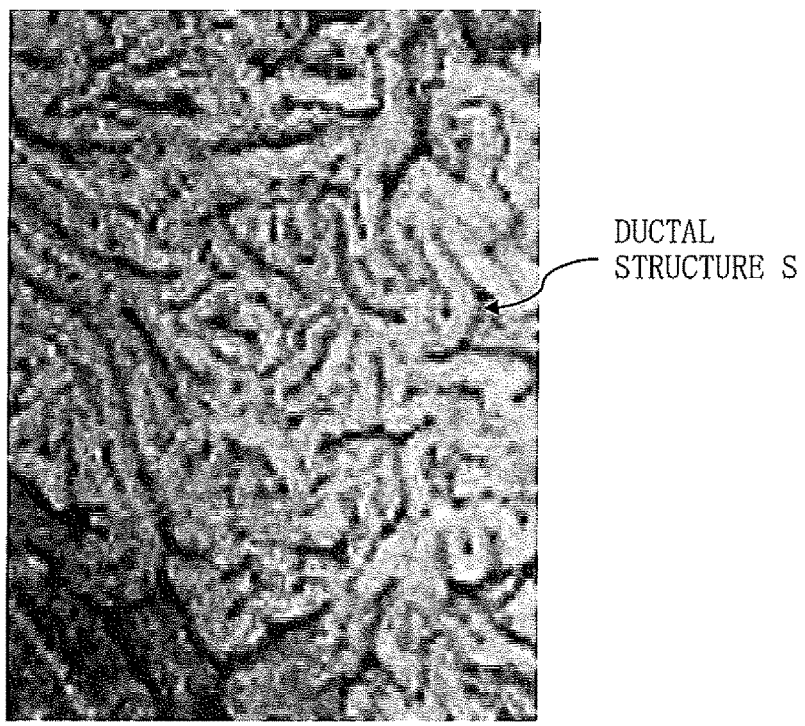
FIG. 18A illustrates an example of a dye-sprayed image captured in the magnified observation.
Figure 18B:
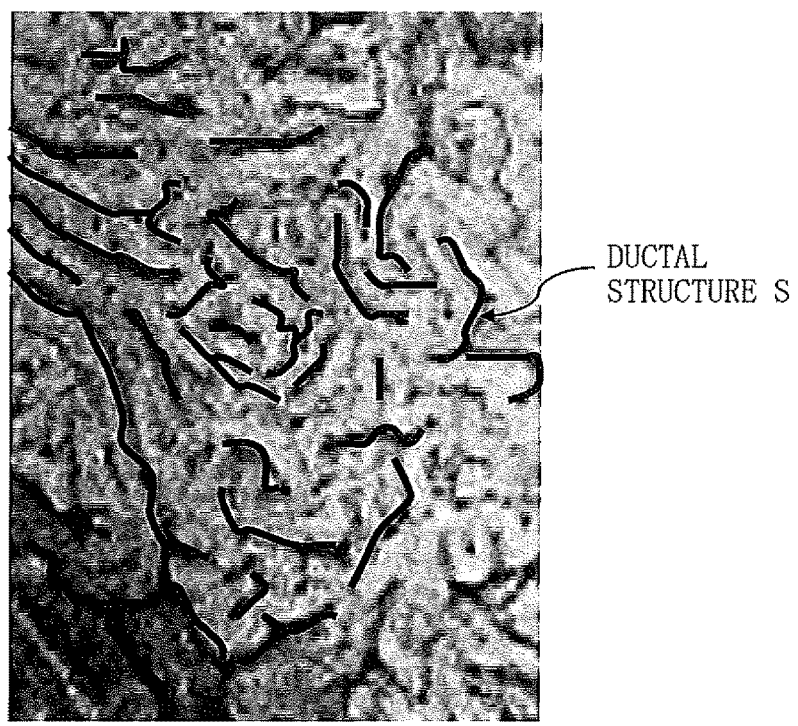
FIG. 18B is an explanatory image view in which black thick lines indicate a ductal structure of FIG. 18A.

18A, a dye-sprayed image in which the ductal structure S is enhanced is displayed on the monitor 18. Note that, in FIG. 18B, the black thick lines indicate the ductal structure S for comparison.

The doctor interprets the state of the ductal structure S in the dye-sprayed image displayed on the monitor 18, to determine whether the potential lesion is a lesion or a non-lesion. Note that the sprayed dye must be washed out after the observation of the dye-sprayed image. The observation of the dye-sprayed image is the last resort used in the case where the ductal structure S is not clear enough for the interpretation of the second special image.

Second Embodiment

Figure 19:
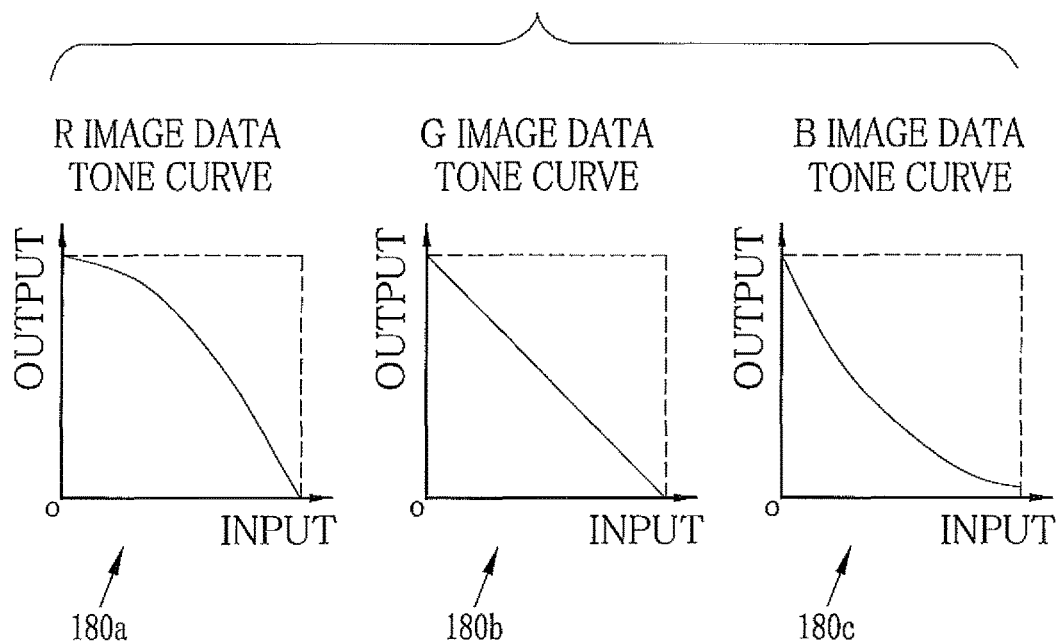
FIG. 19 illustrates graphs of tone curves for the RGB image data, which are used for a tone reversal process of a second embodiment.

In the first embodiment, the tone reversal process made the ductal structure conspicuous, as if the indigo has been sprayed thereon. Additionally, the tone reversal process of the second embodiment makes the color of the mucous membrane close to a color obtained by the image capture using white light and makes the color of the ductal structure closer to the color of the indigo than that in the first embodiment. In the second embodiment, the RGB image data of the vessel-suppressed image is inputted and the tone is reversed based on tone curves 180a to 180c for the RGB image data shown in FIG. 19. Thereby the RGB image data of the suppressed-and-reversed image is outputted.

The tone curve 180a for the R image data is convex-shaped, so that the outputted R image data is slightly greater than the inputted R image data, in intermediate values. The tone curve 180c for the B image data is concave-shaped, so that the outputted B image data is slightly smaller than the inputted B image data, in intermediate values. The tone curve 180b for the G image data is linear-shaped, so that the balance between input and output of an intermediate value is substantially maintained. Hence, in the suppressed-and-reversed image in which the tone-reversed RGB image data is combined, the color of the mucous membrane, most of which is at the intermediate values, is reddish. The reddish color of the mucous membrane in the suppressed-and-reversed image is substantially the same as that of an image captured using the white light.

The tone curve 180c for the B image data is defined to make a shadow slightly brighter than it is supposed to be, in a case where a highlighted portion (that is, the ductal structure S) of the inputted B image data is outputted as the shadow after the tone reversal. Thereby, the color of the ductal structure becomes bluish in the suppressed-and-reversed image and is close to the color of the indigo.

Figure 20:
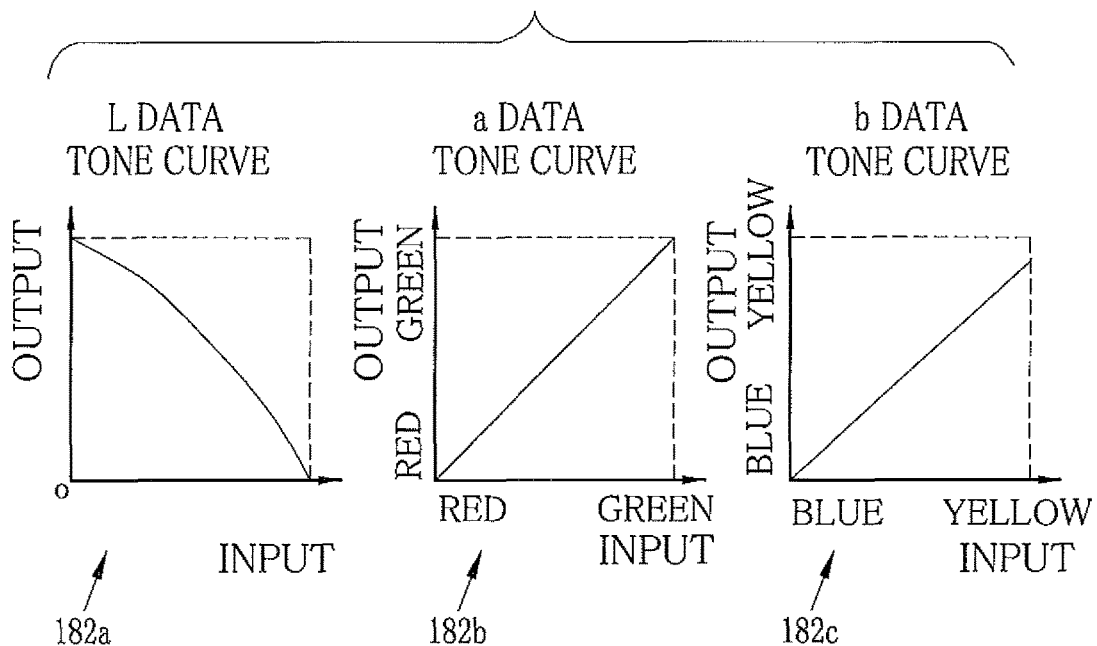
FIG. 20 illustrates graphs of tone curves for the Lab data, which are used for the tone reversal process of the second embodiment.

Note that tone curves 182a to 182c shown in FIG. 20 are used to reverse the tones of the RGB image data of the vessel-suppressed image through the Lab conversion. The tone curve 182a for the L data is convex-shaped, so that the outputted L data is slightly greater than the inputted L data, in intermediate values. The tone curve 182b for the "a" data and the tone curve 182c for the "b" data are linear-shaped, so that the balance between the input and the output of an intermediate value is maintained. The tone curve 182c for the "b" data is defined such that a yellowish color of the inputted "b" data becomes close to blue. Hence, in the suppressed-and-reversed image, after the RGB conversion of the L data, the "a" data, and the "b" data, the color of the mucous membrane, most of which is at the intermediate values, is close to the color of the mucous membrane captured with the white light and the color of the ductal structure is close to the color of the indigo.

In the first and second embodiments, a simultaneous method, in which the color image signals necessary for each mode are obtained simultaneously with a color image sensor, is employed. Alternatively, a frame sequential method may be employed to implement the present invention. In the frame sequential method, image signals necessary for each mode are obtained sequentially with a monochrome image sensor.

Figure 21:
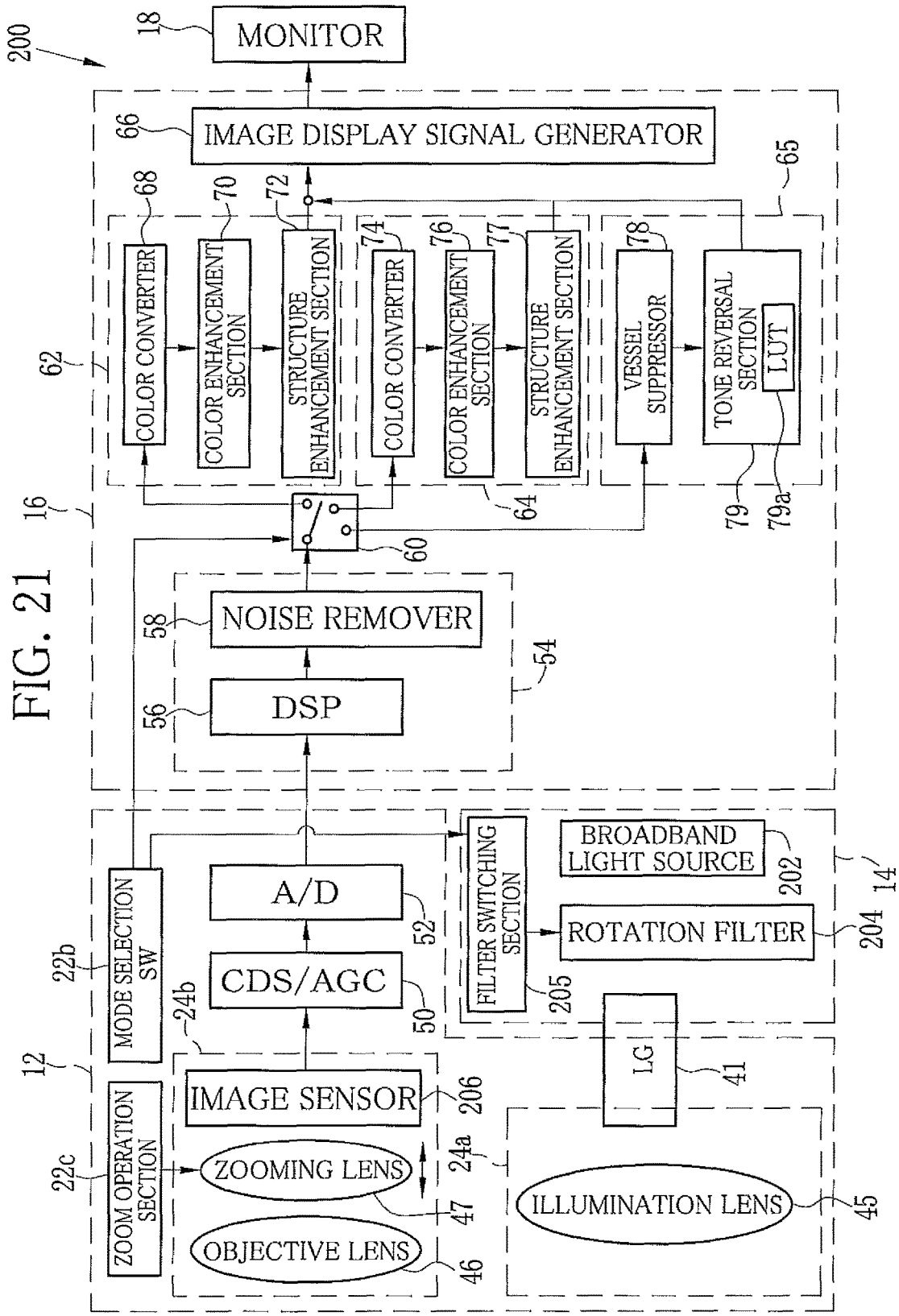
FIG. 21 is a block diagram illustrating configuration of an endoscope system of a frame sequential method.

As shown in FIG. 21, the light source device 14 of an endoscope system 200 of the frame sequential method comprises a broadband light source 202, a rotation filter 204, and a filter switching section 205, instead of the blue laser 34, the blue-violet laser 36, and the light source controller 40. The illuminating optical system 24a of the endoscope 12 is not provided with the phosphor 44. The imaging system 24b comprises a monochrome image sensor 206 with no color filters, instead of the color image sensor 48. Other than those, the endoscope system 200 is similar to the endoscope system 10 of the first embodiment.

The broadband light source 202 is a xenon lamp, a white LED, or the like and emits the white light in a wavelength range from blue to red. The rotation filter 204 comprises a normal mode filter 208 on an inner side and a special mode filter 209 on an outer side (see FIG. 22). The filter switching section 205 moves the rotation filter 204 in a radial direction. In a case where the mode is set to the normal mode by the use of the mode selection SW 22b, the filter switching section 205 inserts the normal mode filter 208 of the rotation filter 204 into a light path of the white light. In a case where the mode is set to the first or the second special mode by the use of the mode selection SW 22b, the filter switching section 205 inserts the special mode filter 209 of the rotation filter 204 into the light path of the white light.

Figure 22:
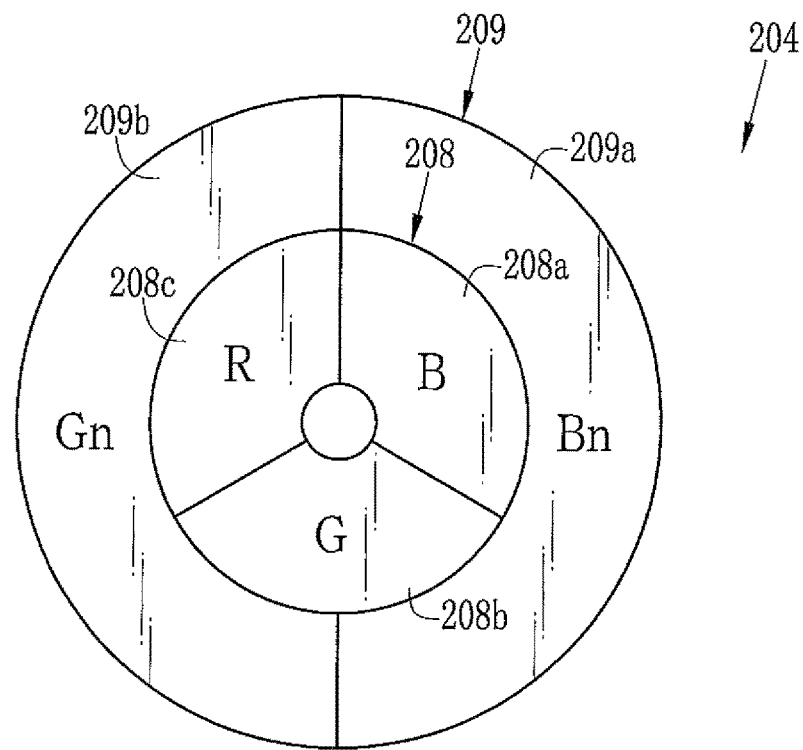
FIG. 22 is a plan view of a rotation filter.

As shown in FIG. 22, the normal mode filter 208 comprises a B filter 208a, a G filter 208b, and an R filter 208c in a circumferential direction. The B filter 208a transmits blue light of the white light. The G filter 208b transmits green light of the white light. The R filter 208c transmits red light of the white light. Hence, in the normal mode, the blue light, the green light, and the red light is applied sequentially to the observation object as the rotation filter 204 is rotated.

The special mode filter 209 comprises a Bn filter 209a and a Gn filter 209b in the circumferential direction. The Bn filter 209a transmits blue narrowband light with the center wavelength of 415 nm of the white light. The Gn filter 209a transmits green narrowband light with the center wavelength of 540 nm of the white light. Hence, in the special mode, the blue narrowband light and the green narrowband light is alternately applied to the observation object as the rotation filter 204 is rotated.

In the normal mode, the monochrome image sensor 206 of the endoscope system 200 of the frame sequential method captures an image of the observation object every time the blue light, the green light, or the red light is applied to the observation object. Thereby RGB image signals of three colors are obtained. The normal image is produced based on the RGB image signals, in a manner similar to the first embodiment.

In the first and the second special modes, the monochrome image sensor 206 captures an image of the observation object every time the blue narrowband light or the green narrowband light is applied to the observation object. Thereby a Bn image signal and a Gn image signal are obtained. Based on the Bn image signal and the Gn image signal, the first and the second special images are produced. Note that, unlike the first and second embodiments, the Bn image signal is assigned to the B image data and the G image data, and the Gn image signal is assigned to the R image data. Thereby the first special image is produced. Other than that, the first special image is produced in a manner similar to the first and second embodiments.

In producing the second special image, the Bn image signal is assigned to the B image data and the G image data, and the Gn image signal is assigned to the R image data, unlike the first and second embodiments. Thereby the base image is produced. The Bn image signal, instead of the B image signal, is used for producing the pre-suppression image. Other than that, the second special image is produced in a manner similar to the first and second embodiments.

Note that, in the above embodiments, the tone reversal process is performed on the vessel-suppressed image, in which the display of the blood vessels is suppressed. Thereby the suppressed-and-reversed image is produced. Conversely, the process for suppressing the display of the blood vessels may be performed on the tone-reversed image, in which the tone is reversed, to produce the suppressed-and-reversed image.

Note that, in the above embodiments, the capillary vessels are extracted by performing the frequency filtering process on the B image signal. The method for extracting the capillary vessels is not limited to this. For example, the capillary vessels may be extracted from a B/G image composed of a luminance ratio B/G between the B image signal and the G image signal. In this case, a pixel with the luminance ratio B/G of less than a predetermined value is extracted as a pixel corresponding to the capillary blood vessel(s) from the B/G image. This is because the balance between the B image signal and the G image signal is constant in the pixel corresponding to the mucous membrane while the luminance ratio B/G of the pixel corresponding to the capillary vessel (s) is lower than that of the pixel corresponding to the mucous membrane. The value of the B image signal is reduced due to the hemoglobin absorbing the blue component.

Note that the phosphor 44 is provided in the distal portion 24 of the endoscope 12 in the first embodiment. Instead, the phosphor 44 may be provided in the light source device 14. In this case, the phosphor 44 is preferably provided between the light guide 41 and the blue laser 34.

Note that the endoscope system 10 of the above-described simultaneous method uses the B image signal to produce the suppressed-and-reversed image. The B image signal is a narrowband signal in which information of narrowband wavelengths of the blue laser beams and the blue-violet laser beams are included. The endoscope system 200 of the above-described frame sequential method uses the Bn image signal to produce the suppressed-and-reversed image. The Bn image signal is a narrowband signal in which information of narrowband wavelengths of the blue narrowband light is included. Instead, a blue narrowband image signal may be generated by spectral calculation based on a broadband image such as a white light image, to produce the suppressed-and-reversed image. The blue narrowband image signal has a considerable amount of information related to the ductal structure.

Figure 23:
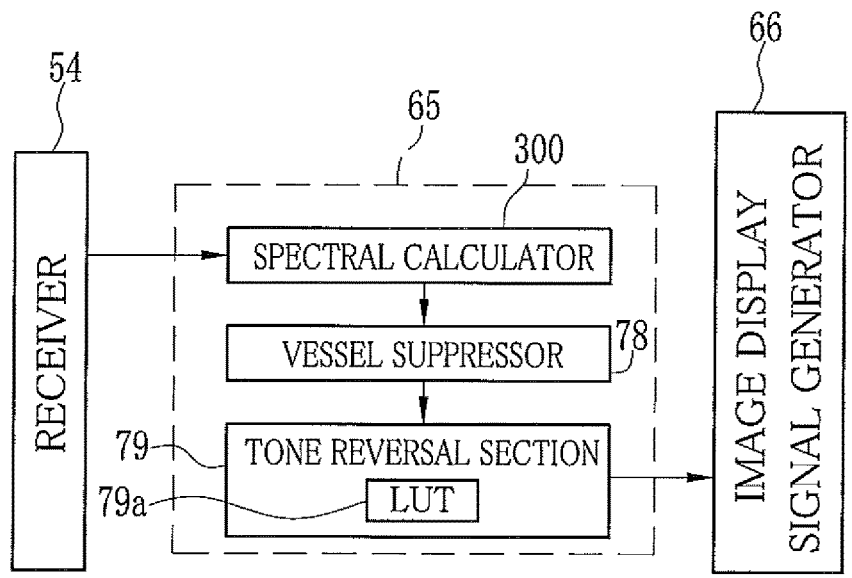
FIG. 23 is a block diagram of a second special image processor having a spectral calculator.
Figure 24A:
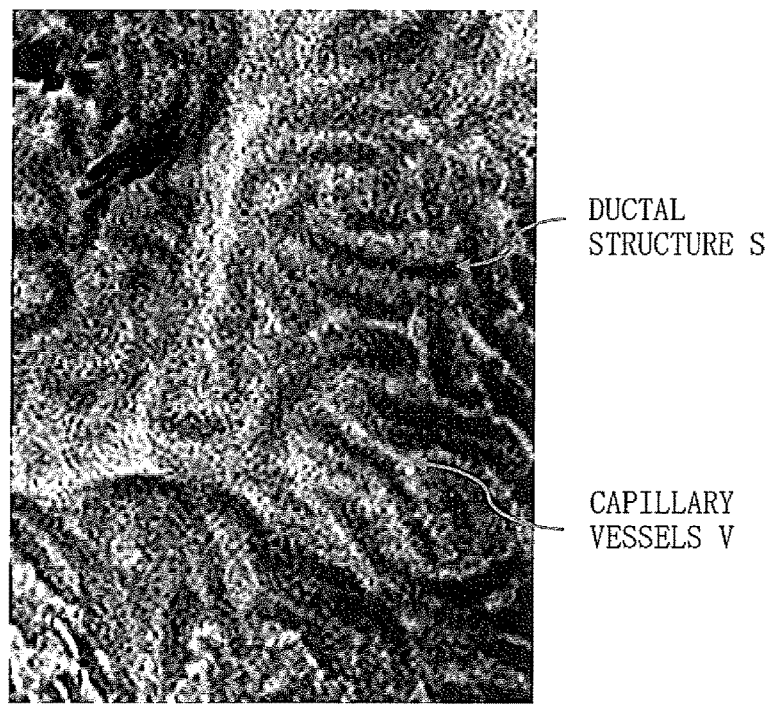
FIG. 24A illustrates an example of a conventional reversed narrowband image captured in the magnified observation.
Figure 24B:
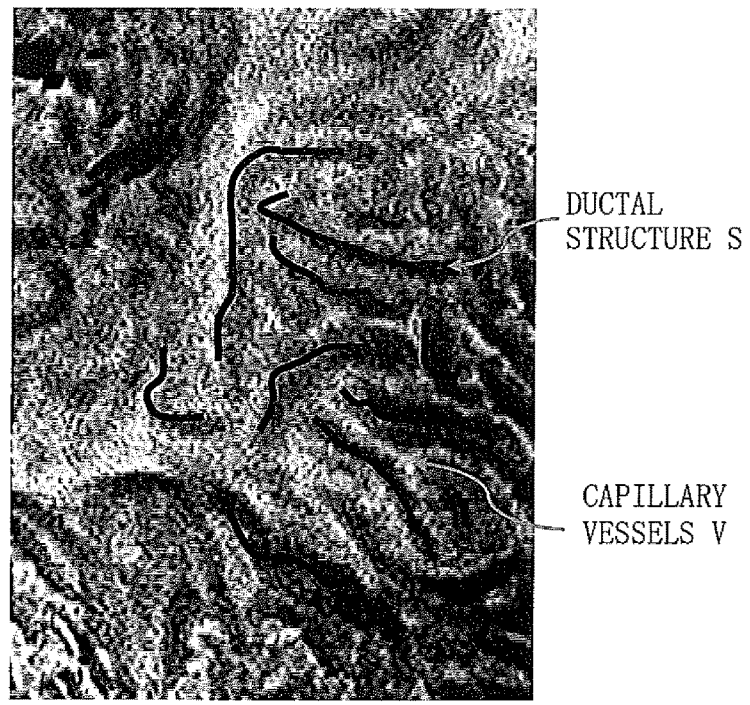
FIG. 24B is an explanatory image view in which black thick lines indicate a ductal structure of FIG. 24A.

In this case, in the second special mode, the endoscope system 10 of the simultaneous method applies the white light instead of the special light. As shown in FIG. 23, a spectral calculator 300 is provided between the receiver 54 and the vessel suppressor 78. The spectral calculator 300 performs a spectral calculation process based on the RGB image signals obtained by the image capture with the illumination of the white light. Thereby a blue narrowband image signal is generated. The blue narrowband image signal (for example, a blue narrowband image signal having information of wavelength of 415 nm) has a considerable amount of information related to the ductal structure S. A method of the spectral calculation disclosed in Japanese Patent Laid-Open Publication No. 2003-093336 is used. The suppressed-and-reversed image is produced based on the blue narrowband image signal, which is produced by the spectral calculator 300, and the G and R image signals, in steps similar to those in the above embodiments. Note that the white light may be generated using the phosphor 44 or emitted from a broadband light source such as a xenon lamp.

Note that, in the above embodiments, the image processing of the present invention is performed during the observation using the endoscope. The image processing may be performed on an endoscope image stored in a storage section of the endoscope system, after the observation using the endoscope. In this case, the endoscope system needs to comprise an image input section for inputting the image to the processor device from the storage section.

Various changes and modifications are possible in the present invention and may be understood to be within the present invention.

What is claimed is:

1. An image processing device comprising:
    an image input section for inputting a first image, the first image including a first structure brighter than a mucous membrane and a second structure darker than the mucous membrane; and
    an image processor for performing a suppression process and a tone reversal process on the first image to produce a second image, a display of the second structure being suppressed in the suppression process, the first structure being darker than the mucous membrane in the second image, and the mucous membrane having substantially the same brightness as the second structure in the second image,
    wherein the image processor extracts the first structure and the second structure from at least one channel of three RGB channels which constitute the first image for generating a structure-extracted image signal in which a signal value is different between the first structure and the second structure in positive or negative to the mucous membrane, converts a negative input value of the structure-extracted image signal to a positive output value and converts a positive input value of the structure-extracted image signal to a positive or zero output value for generating a pre-suppression image, adds the pre-suppression image to at least one channel of the three RGB channels which constitute the first image for generating a second structure-suppressed image, and reverses gradation of RGB image data of the second structure-suppressed image for generating RGB image data of the second image.

2. The image processing device of claim 1, wherein the image processor performs the suppression process on the first image, and performs the tone reversal process on a suppression-processed first image to make the first structure darker than the mucous membrane.

3. The image processing device of claim 2, wherein the first image is represented by RGB image data, and
    the image processor reverses a tone of suppression-processed RGB image data.

4. The image processing device of claim 2, further comprising a separator for separating the suppression-processed first image into brightness data and color data, the brightness data having brightness information, the color data having color information, and wherein the image processor reverses a tone of the brightness data.

5. The image processing device of claim 1, wherein the image processor performs the suppression process on the first image, and performs the tone reversal process on a suppression-processed first image to make the first structure darker than the mucous membrane and to make a color of the first structure close to a color of a bluish dye.

6. The image processing device of claim 5, wherein the image processor makes a color of the mucous membrane close to a color of the mucous membrane illuminated with white light.

7. The image processing device of claim 6, wherein
the first image is represented by RGB image data, and
the image processor reverses a tone of suppression-processed R image data so as to make an intermediate value of the suppression-processed R image data bright, and reverses a tone of suppression-processed B image data so as to make an intermediate value of the suppression-processed B image data dark, and reverses the tones such that dark portions become bright after the tone reversal process.

8. The image processing device of claim 6, further comprising a separator for separating the suppression-processed first image into brightness data and color data, the brightness data having brightness information, the color data having color information, and
wherein the image processor reverses a tone of the brightness data so as to make an intermediate value of the brightness data bright, and changes the color data so as to make an yellowish color close to blue.

9. The image processing device of claim 5, wherein the bluish dye is an indigo.

10. The image processing device of claim 1, wherein first image has a blue narrowband image and the blue narrowband image includes the first and the second structures.

11. The image processing device of claim 1, further comprising
an image magnifier for magnifying the first and the second structures, and
wherein the first image is obtained in magnified observation using the image magnifier.

12. The image processing device of claim 1, wherein the first structure is a ductal structure and the second structure is capillary vessels.

13. The image processing device of claim 1,
wherein the image processor extracts a frequency band component corresponding to the second structure from the first image by a frequency filtering process for generating the second structure-extracted image signal.

14. The image processing device of claim 1,
wherein the image processor includes a LUT, the second structure-extracted image signal being inputted to the LUT, and the LUT outputting the pre-suppression image, and
wherein the LUT outputs a positive value in a case where the second structure-extracted image signal with a negative value is inputted.

15. A method for operating an endoscope system comprising the steps of:
inputting a first image from an image input section, the first image including a first structure brighter than a mucous membrane and a second structure darker than the mucous membrane; and
performing a suppression process and a tone reversal process on the first image to produce a second image, by a suppression and reversal section, a display of the second structure being suppressed in the suppression process, the first structure being darker than the mucous membrane in the second image, and the mucous membrane having substantially the same brightness as the second structure in the second image,
wherein the suppression and reversal processes extract the first structure and the second structure from at least one channel of three RGB channels which constitute the first image for generate a structure-extracted image signal in which a signal value is different between the first structure and the second structure in positive or negative to the mucous membrane, converts a negative input value of the structure-extracted image signal to a positive output value and converts a positive input value of the structure-extracted image signal to a positive or zero output value for generating a pre-suppression image, add the pre-suppression image to at least one channel of the three RGB channels which constitute the first image for generating a second structure-suppressed image, and reverse gradation of RGB image data of the second structure-suppressed image for generating RGB image data of the second image.

* * * * *